(12) United States Patent
Thompson et al.

(10) Patent No.: US 11,270,098 B2
(45) Date of Patent: Mar. 8, 2022

(54) CLUSTERING METHODS USING A GRAND CANONICAL ENSEMBLE

(71) Applicant: THE UNITED STATES OF AMERICA, AS REPRESENTED BY THE SECRETARY, DEPARTMENT OF HEALTH AND HUMAN SERVICES, Silver Spring, MD (US)

(72) Inventors: Elaine Ellen Thompson, Silver Spring, MD (US); Vahan Simonyan, Rockville, MD (US); Malcolm Moos, Jr., Silver Spring, MD (US)

(73) Assignee: THE UNITED STATES OF AMERICA, AS REPRESENTED BY THE SECRETARY, DEPARTMENT OF HEALTH AND HUMAN SERVICES, Silver Spring, MD (US)

( * ) Notice: Subject to any disclaimer, the term of this patent is extended or adjusted under 35 U.S.C. 154(b) by 105 days.

(21) Appl. No.: 16/764,557

(22) PCT Filed: Nov. 15, 2018

(86) PCT No.: PCT/US2018/061348
§ 371 (c)(1),
(2) Date: May 15, 2020

(87) PCT Pub. No.: WO2019/099716
PCT Pub. Date: May 23, 2019

(65) Prior Publication Data
US 2020/0311384 A1    Oct. 1, 2020

Related U.S. Application Data

(60) Provisional application No. 62/587,288, filed on Nov. 16, 2017.

(51) Int. Cl.
*G06K 9/00* (2006.01)
*G06T 7/00* (2017.01)

(52) U.S. Cl.
CPC ....... *G06K 9/00147* (2013.01); *G06K 9/0014* (2013.01); *G06T 7/0012* (2013.01); *G06T 2207/30024* (2013.01)

(58) Field of Classification Search
None
See application file for complete search history.

(56) References Cited

U.S. PATENT DOCUMENTS 8,849,575 B2   9/2014  Gustaffson et al.
8,916,530 B2   12/2014 Shanahan et al.
(Continued)

FOREIGN PATENT DOCUMENTS

| JP | H05072197 A | 3/1993 |
|----|----|----|
| WO | WO 2001/067061 A2 | 9/2001 |
| WO | WO 2005/114458 A1 | 12/2005 |

OTHER PUBLICATIONS

International Search Report, International Application No. PCT/US2018/061348, filed Nov. 15, 2018, 3 pages (Feb. 13, 2019).
(Continued)

*Primary Examiner* — Soo Jin Park
(74) *Attorney, Agent, or Firm* — Klarquist Sparkman, LLP

(57) ABSTRACT

Methods are disclosed for clustering biological samples and other objects using a grand canonical ensemble. A biological sample is characterized by data attributes from varying sources (e.g. NGS, other types of high-dimensional cytometric data, observed disease state) and of varying data types (e.g. Boolean, continuous, or coded sets) organized as vectors (as many as $10^9$) having as many as $10^6$, $10^9$, or more components. The biological samples or observational data are modeled as particles of a grand canonical ensemble
(Continued)

which can be variably distributed among partitions. A pseudo-energy is defined as a measure of inverse similarity between the particles. Minimization of grand canonical ensemble pseudo-energy corresponds to clustering maximally similar particles in each partition, thereby determining clusters of the biological samples. The sample clusters can be used for feature discovery, gene and pathway identification, and development of cell based therapeutics, or for other purposes. Variations and additional applications are disclosed.

20 Claims, 13 Drawing Sheets

(56) References Cited

U.S. PATENT DOCUMENTS

| | | | |
|---|---|---|---|
| 9,367,683 | B2 | 6/2016 | Kolacinski et al. |
| 9,495,515 | B1 | 11/2016 | Kennedy et al. |
| 2004/0088116 | A1 | 5/2004 | Khalil et al. |
| 2004/0267509 | A1 | 12/2004 | Brunner et al. |
| 2009/0094012 | A1 | 4/2009 | Clark |
| 2015/0178383 | A1 | 6/2015 | Corrado et al. |

OTHER PUBLICATIONS

Written Opinion of the International Searching Authority, International Application No. PCT/US2018/061348, filed Nov. 15, 2018, 1 page (Feb. 13, 2019).

Allen, "Introduction to Molecular Dynamics Simulation", published in Computational Soft Matter: From Synthetic Polymers to Proteins, Lecture Notes, John von Neumann Institute for Computing, NIC Series, vol. 23, pp. 1-28 (Feb. 2004).

Angermueller et al., "Supplementary Figure 10: Clustering analysis of transcriptome and methylation data from 61 serum ESCs.", from "Parallel single-cell sequencing links transcriptional and epigenetic heterogeneity", Nature Methods 13, pp. 229-232; Supplementary Fig. 10 available from http://www.nature.com/nmeth/journal/v13/n3/fig_tab/nmeth.3728_SF10.html, 2 pages (Jan. 11, 2016).

Boinepalli, "Grand canonical molecular dynamics", J. Chem. Phys. 119, 12769, pp. 1-8 (Dec. 2003).

Cai, "Handout 9. NPT and Grand Canonical Ensembles", ME346A Introduction to Statistical Mechanics, Stanford University, available from http://micro.stanford.edu/~caiwei/me334/Chap9_NPT_Grand_Canonical_Ensemble_v04.pdf, pp. 1-12 (Jan. 2011).

Getz et al., "Coupled two-way clustering analysis of breast cancer and colon cancer gene expression data", Bioinformatics, vol. 19 No. 9, pp. 1079-1089 (Jun. 2003).

Grun et al., "Extended Data Figure 2: Clustering reveals major transcriptome differences between intestinal cells.", from "Single-cell messenger RNA sequencing reveals rare intestinal cell types", Nature 525, pp. 251-255; Extended Data Figure 2 available from http://www.nature.com/nature/journal/v525/n7568/fig_tab/nature14966_SF2.html, 2 pages (Sep. 10, 2015).

McLachlan et al., "Clustering of High-Dimensional and Correlated Data", pp. 1-9, also published as McLachlan et al., "Clustering of High-Dimensional and Correlated Data", Proceedings of the $6^{th}$ Conference of the Classification and Data Analysis Group of the Societa Italiana di Statistica (Dec. 2009).

Mishra et al., "Clustering Algorithms: Brief Review in Bioinformatics", International Journal of Science and Research, vol. 6 Issue 1, pp. 1012-1019 (Jan. 2017).

Musiani et al., "Molecular Mechanics/Coarse-grain simulations as a structural prediction tool for GPCRs/ligand complexes", pp. 1-22, also published as Musiani et al., "Molecular Mechanics/Coarse-grain simulations as a structural prediction tool for GPCRs/ligand complexes", In Silico Drug Discovery and Design: Theory, Methods, Challenges, and Applications, CRC Press, pp. 337-352 (Aug. 2015).

Samusik et al., "Automated mapping of phenotype space with singe-cell data", Nature Methods 13, pp. 493-496 (May 2016).

Sekerka, "Thermal Physics: Thermodynamics and Statistical Mechanics for Scientists and Engineers", Elsevier, pp. 1-588 (Aug. 2015).

Shell, "Monte Carlo simulations in other ensembles", ChE 210D Lecture Notes, University of California, Santa Barbara, available from https://engineering.ucsb.edu/~shell/che210d (May 2012).

Simonyan et al., "High-performance integrated virtual environment (HIVE): a robust infrastructure for next-generation sequence data analysis", Database, vol. 2016, article ID baw022, pp. 1-16 (Mar. 2016).

Steinbach et al., "The Challenges of Clustering High Dimensional Data", pp. 1-33, also published as Steinbach et al., "The Challenges of Clustering High Dimensional Data", in New Vistas in Statistical Physics—Applications in Econophysics, Bioinformatics, and Pattern Recognition, Springer-Verlag, pp. 273-309 (2004).

Tetko et al., "Super paramagnetic clustering of protein sequences", BMC Bioinformatics 6:82, pp. 1-13 (Apr. 2005).

Wang et al., "STAR: an integrated solution to management and visualization of sequencing data", Bioinformatics, vol. 29 No. 24, pp. 3204-3210 (Sep. 2013).

Wang et al., "Robust High-dimensional Bioinformatics Data Streams Mining by ODR-ioVFDT", Scientific Reports 7:43167, pp. 1-12 (Feb. 2017).

CLUSTERING METHODS USING A GRAND CANONICAL ENSEMBLE

CROSS-REFERENCE TO RELATED APPLICATIONS

This is the U.S. National Stage of International Application No. PCT/US2018/061348, filed Nov. 15, 2018, which was published in English under PCT Article 21(2), which in turn claims the benefit of U.S. Provisional Application No. 62/587,288, filed Nov. 16, 2017. The provisional application is incorporated in its entirety by reference herein.

BACKGROUND

Bioinformatics and genomics offer tremendous potential to revolutionize medicine, through the development of cell-based therapeutics (CBT) and personalized medicine. With the use of next-generation sequencing (NGS), microarrays, cytometry, and other techniques, cell characterization can include DNA sequence, mRNA transcriptome, proteomic information, morphologic features, and/or other types of data. Of particular interest is the identification of cell and gene features that are associated with aspects of cell functioning and disease states.

Clustering algorithms, principal component analysis (PCA), discriminant analysis, and other similar techniques have been used to explore cell data. However, NGS biological cell data has certain characteristics that render existing clustering and classification techniques unsuitable: dimensionality, heterogeneity, and discontinuity in particular. The very high dimensionality of a cell description based on methods such as single cell mRNAseq leads to a breakdown of distance or density metrics on which many techniques rely. The heterogeneous and often bimodal data encountered in cell descriptions are not statistically well-characterized, which limits applicability of PCA, Support Vector Machine (SVM), discriminant analysis, and other dimensionality reduction techniques. Furthermore, the dimensionality of the cell descriptions vastly exceeds the number of available samples in many cases. As a result, covariance or scattering matrices are very sparse, which limits the applicability of classification techniques based on linear algebra. From a computation perspective, these issues can be manifested as problems with numerical instability. In addition, conventional techniques also suffer from unfavorable scaling with dimension, which can lead to excessive computation times for high-dimensional NGS data.

Thus, conventional techniques are unable to provide unsupervised clustering or classifier discovery for some rich cell descriptions available today. Accordingly, there is ample opportunity to improve clustering and classification technology for high-dimensional data from biological samples.

SUMMARY

In certain examples, the detailed description is directed to various innovative technologies for clustering data using a grand canonical ensemble, the particles of which can represent respective samples. The phases of the grand canonical ensemble are partitions into which the particles can be disposed. Through optimization or iterative improvement, a pseudo-energy function based on particle similarity, on the partitions can be minimized, leading to partitions containing maximally similar particles; the selected partitions contain the desired particle (or, sample) clusters. Optimization can use a randomized method such as Monte Carlo (MC), with a Metropolis criterion, and can also employ deterministic evolution of the ensemble.

In certain examples, biological samples can be classified. Data vectors characterizing respective biological samples are formed, and one or more measures representative of similarity between data vectors are defined. An optimization is performed on a grand canonical ensemble having a plurality of particles variably distributed among one or more partitions, wherein the particles represent or are represented by respective data vectors. From the optimization, a set of selected partitions is determined, in which each selected partition has substantially maximized similarity between the data vectors of the particles in the partition. Optimizing the partitions leads to classification or clustering of the biological samples. The biological samples can be single cells, each biological sample's data vector can include components representing corresponding attributes of the biological sample, and/or the optimization can be directed to minimization of pseudo-energy measure(s) in at least one partition of the grand canonical ensemble. Example attributes in a data vector can include NGS data, such as a gene expression or a gene mutation, other cytometric data, medical record data, a disease state attribute, and/or other observable attributes of the sample. A pseudo-energy can be an inverse similarity function defined pairwise on two data vectors and aggregated over all vector pairs in a partition. Alternatively, a pseudo-energy function can be defined such that energy across more than two vectors is aggregated, where more distant vectors have a smaller contribution to the aggregate energy. A wide range of similarity measures and weighting functions can be used. The optimization can use a variety of randomized and/or deterministic operations, both intra-partition and inter-partition, and partitions can be created or emptied; the operations can be applied on particles and/or on component indices of the data vectors; a Metropolis criterion and/or simulated annealing can be employed to drive the grand canonical ensemble to a desired minimum pseudo-energy state. The optimization or improvement can be performed in various modes, with varying reset functions or states. In examples, a group of biological samples corresponding to one of the selected partitions can be selected; features can be extracted using linear discriminant analysis or another technique; genes and/or pathways can be identified from the extracted features; feature sets corresponding to desired biological or therapeutic characteristics can be used to guide optimized manufacture and testing of a cell-based therapy.

In certain examples, a cell-based therapy can be developed. Data vectors characterizing respective biological samples are formed. Each NGS based data vector may have as many as $10^6$ components, including continuous measures such as genetic expressions and binary state variables such as Single Nucleotide Variant (SNV) presence or absence. When samples are from multiple sources a component representing the source is included. When known, a component representing a disease state or efficacy of the corresponding biological sample is included. A pair-wise pseudo-energy is defined, which is dependent on similarity between two data vectors. In further examples, the pseudo-energy can be distance based, or can depend on data vector dissimilarity, or can depend on adjacent data vectors, or on more than two data vectors. A grand canonical ensemble having one or more partitions and multiple particles is configured, wherein each particle is identified with a respective data vector of a biological sample. A Monte Carlo procedure with simulated annealing is performed on the ensemble, directed to minimization of a particle pseudo-energy in each of multiple partitions. The particles are variably disposed within a variable number of the partitions. The partition pseudo-energy of a partition includes a sum of pairwise pseudo-energies over pairs of data vectors of the particles in the partition. From the optimization, a set of selected partitions is determined, each selected partition having substantially minimized pseudo-energy. For each selected partition, a cluster is formed from the biological samples associated with the particles in that selected partition. Features of a first cluster are extracted using a linear discriminant analysis technique, and the extracted features are used as a basis to determine characteristics of subpopulations of cells. Those characteristics are used to define cell populations within the sample, compare samples between disease states or differing efficacy, and then to develop cell-based therapies using the characteristics as quality attributes of the cells. In NGS studies, the ensemble can include as many as $10^8$ components, including components representing gene mutation data.

An optimization is performed on a grand canonical ensemble having a plurality of particles variably distributed among one or more partitions, wherein the particles are identified with respective data vectors. From the optimization, a set of selected partitions is determined, in which each selected partition has substantially maximized similarity between the data vectors of the particles in the partition. Optimizing or improving the partitions leads to classification or clustering of the biological samples.

In additional embodiments, computer-implemented methods, computer systems, and computer readable media are provided.

The foregoing and other features and advantages of the disclosed technologies will become more apparent from the following detailed description of several embodiments which proceeds with reference to the accompanying figures.

DETAILED DESCRIPTION

I. Summary of Terms

Figure 1:
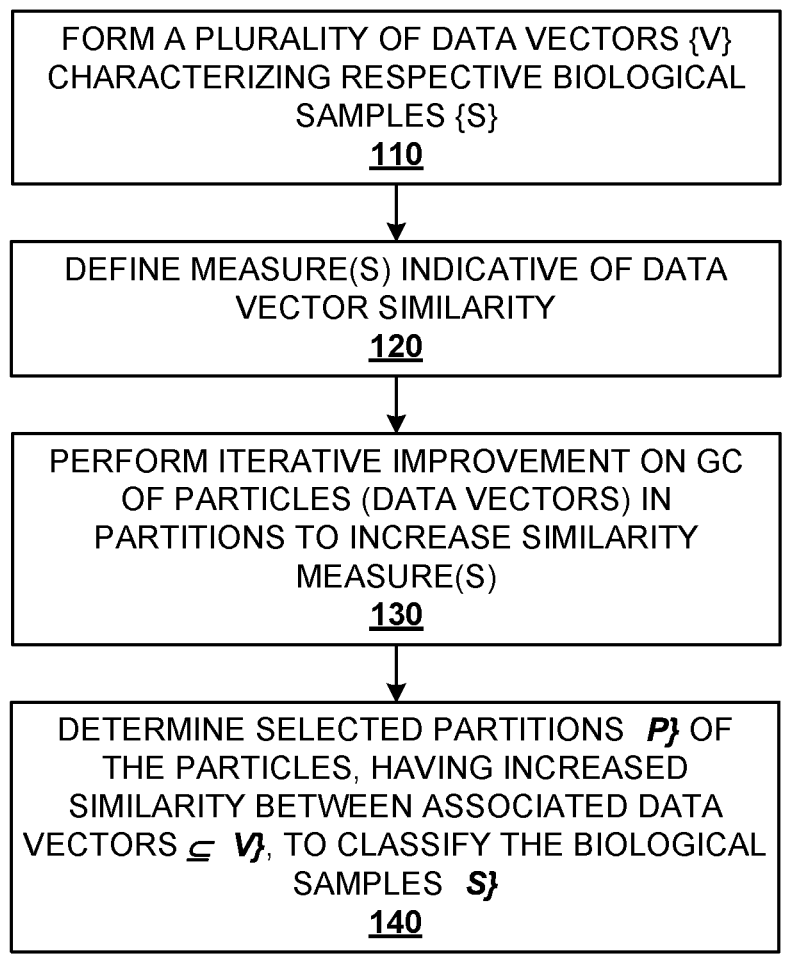
FIG. 1 is a flowchart depicting an example method for classifying biological samples (e.g., individual cells), using a Grand Canonical ensemble of particles representing data attributes of respective samples, according to disclosed technology.

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

About: Plus or minus 5% from a set amount. For example, "about 5" refers to 4.75 to 5.25. A ratio of "about 5:1" refers to a ratio of from 4.75:1 to 5.25:1.

Artifact: An artifact is something observed in a computation or scientific investigation that is not naturally present but occurs as a result of the computational or investigative process.

Biological sample: A sample obtained from an individual, from a tissue culture, or from a biological specimen. As used herein, biological samples include all clinical and experimental samples containing RNA (including mRNA) and/or genomic DNA (such as cell-free genomic DNA), including, but not limited to, cells, tissues, and bodily fluids, such as: blood, derivatives and fractions of blood (such as serum or plasma), buccal epithelium, saliva, urine, stools, bronchial aspirates, sputum, biopsy (such as tumor biopsy), and CVS (Chorionic Villus Sampling) samples. A "biological sample" obtained or derived from an individual includes any such sample that has been cultured or otherwise processed in any suitable manner (for example, processed to isolate genomic DNA for bisulfite treatment) after being obtained from the individual.

Binary variable: A binary variable is any object in a computation or data structure that can take on exactly two values or states, such as True or False, zero or one, or male or female. The available values for a binary variable are not limited, but can be any two values or states. A Boolean variable is a special case of a binary variable, where the values are True or False.

Cancer: A cancer is a biological condition in which a malignant tumor or other neoplasm has undergone characteristic anaplasia with loss of differentiation, increased rate of growth, invasion of surrounding tissue, and which is capable of metastasis. A neoplasm is a new and abnormal growth, particularly a new growth of tissue or cells in which the growth is uncontrolled and progressive. A tumor is an example of a neoplasm. Non-limiting examples of types of cancer include lung cancer, stomach cancer, colon cancer, breast cancer, uterine cancer, bladder, head and neck, kidney, liver, ovarian, pancreas, prostate, and rectum cancer.

Categorical Variable: A categorical variable is any object in a computation or data structure that can take one of a limited, fixed number of possible values from a predetermined list, such as red, yellow, or green; benign, malignant, or metastatic; or A, B, C, D or F. The predetermined list can be any length greater than one. The values may be represented as numbers, but no mathematical relationship between the classifications is assumed or implied.

Cell: The basic structural unit of living organisms. Non-limiting examples of cells include T-cells, B-cells, stem cells, neurons, chondrocytes, and tumor cells.

Cell based therapy: Administration of one or more intact living cells to a subject for therapeutic purposes. Non-limiting examples of cell based therapy include administration of T cells to induce T-cell-mediated immunity to an appropriate cancer patient, administration of autologous or heterologous hematopoietic stem cells to a patient with a hematological cancer (with or without bone marrow ablation), administration of mesenchymal stem cells for bone and cartilage regeneration, and administration of neural stem cells for treatment of neurodegenerative disease (such as Alzheimer's disease, Parkinson's disease, Huntington's disease). In some embodiments, the methods provided herein for characterizing and classifying biological samples, such as cells, can be used to identify particular cells and/or types of cells having increased efficacy for treating disease (such as the conditions noted above) in a subject and/or that are less likely to induce an immune response in the subject leading to harmful side effects (such as rejection of the administered cells).

Classification: Classification refers both to the problem of categorizing biological samples or other objects, and to the taxonomy of classes into which the biological samples or other objects are classified once the problem of categorizing has been addressed. Classification as a problem includes both the problems of classifying an existing set of biological samples or other objects, and the problem of determining classifiers by which new biological samples or other objects can be classified; the former problem can but need not include the determination of classifiers.

Cluster: A cluster is a group of biological samples or other objects having at least one similar attribute. In this description, biological samples are described by data vectors, and a measure of similarity can be defined on the data vectors. Generally, on average, a vector of a cluster is more similar to other vectors in its own cluster than to vectors outside its cluster. In examples, a vector, a biological sample, or another object can belong to more than one cluster. Generally, the measure of similarity can be different for different clusters. In this description, the particles (or data vectors or biological samples) of a selected partition can form a cluster.

Coded set: A coded set is a representation of a discrete and finite set of values or states that can be taken by a variable. The corresponding variable is sometimes known as a categorical variable or an enumerated type. The values of the coded set (e.g. 0, 1, 2, 3) can differ from the values or states that they represent (e.g. blood types "0," "A," "B," "AB"). Both binary and categorical variables can be represented with coded sets. A Boolean variable is a special case of a coded set, where true can be represented by 1 and false by 0.

Cytometric Data: Data concerning the characteristics of one or more cells, such as DNA, mRNA, and protein sequence and expression level, cell-surface expression level of a protein, source (e.g., cells from an organ or tumor), disease state (e.g., cells from a subject with a particular disease or condition), etc.

Detecting: To identify the existence, presence, or fact of something. General methods of detecting are known to the skilled artisan and may be supplemented with the techniques disclosed herein.

Diagnosis: The process of identifying a disease (such as cancer) by its signs, symptoms and results of various tests. The conclusion reached through that process is also called "a diagnosis." Forms of testing performed include but are not limited to blood tests, stool tests, medical imaging, urinalysis, endoscopy, biopsy, and epigenetic characterization of genomic DNA.

Disease state: A disease state is an indication of presence, absence, or degree of a disease. The disease state is sometimes a binary variable (present or absent) but can also be a categorical variable (e.g. stage of a cancer) or a continuous variable (e.g. bone density as an indicator or osteoporosis).

DNA (deoxyribonucleic acid): DNA is a long chain polymer which comprises the genetic material of most living organisms. The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, for instance, it is appropriate to generate probes or primers from the reverse complement sequence of the disclosed nucleic acid molecules. There are multiple epigenetic processes (e.g., covalent modifications to chromatin, DNA, or proteins), that can result into alteration of biological processes despite identical DNA sequence.

Feature: As used in this disclosure, a feature is a characteristic common to a plurality of objects (such as biological samples) in a cluster, as distinct from a characteristic of a single object (such as a biological sample) which is preferentially termed a characteristic. A feature need not be common to all members of the cluster. In some examples, a feature is common to a majority of cluster members, while in other examples, a feature is not common to a majority of cluster members.

Grand canonical ensemble: A grand canonical (GC) ensemble is a statistical ensemble (collection of particles in an interacting dynamic system) that is made of ensembles of particles, each describing a particular microstate. The equations driving the equilibrium or energy/particle flux for the GC ensemble are similar in form to the equations that control energy and particle flux of a single ensemble. For example, some grand canonical ensembles can be characterized by a chemical potential $\mu$, and optionally a volume V, a temperature T or any other macroscopic parameter describing the system. GC ensembles can be designed with variable numbers of particles, volume, pressure, and temperature; i.e. grand canonical ensembles can be open, closed, or adiabatic systems. The ensemble can be distributed over one, two, or more phases; the distribution and migration of elements between phases is controlled by one of the macroscopic parameters (e.g. the chemical potential, volume and/or the temperature, etc.) Conventionally, grand canonical ensembles are used for atomic or molecular particles, and can be used to describe atomic or molecular material systems having multiple phases, such as solid or liquid, or macroscopic magnetic domains.

In this disclosure, a grand canonical ensemble is used to describe a plurality of sub-dimensional representations of data vectors representing respective biological samples; that is, a biological sample in a particular GC microstate is analogous to a particle and is represented by a subset of dimensions taken from its data vector. The phases of the grand canonical ensemble are represented by partitions into which zero, one, or more particles (data vectors) can be placed and characterized with the subset of measurements. In lieu of energy, a pseudo-energy is defined as a measure of inverse similarity between data vectors. By using inverse similarity rather than similarity, maximal similarity is mapped to lowest energy, so that improving or optimizing the grand canonical ensemble into a low energy state corresponds to clustering maximally similar data vectors (particles) into each partition. Thus, the grand canonical ensemble algorithm can be used to cluster data vector subcomponents, and by extension cluster the biological samples described by these feature subspaces. A pseudo-temperature (dubbed "temperature" for short in this disclosure) or any macroscopic state parameter controlling the equilibrium or energy flux behavior between partitions can serve as a parameter which controls the probability with which particles move within or between partitions, and thus the vigor with which different states are explored. Changing the pseudo-temperature (or other macroscopic parameter) permits cycles of simulated annealing, increasing the number of solutions discovered over the course of a given simulation. In some embodiments, a parameter (such as pseudo-temperature) controlling probabilities for intra-partition operations can be distinct from other parameters controlling inter-partition operations; the pseudo-temperature and such other parameters can be managed independently.

The chemical potential is the pseudo-energy change when a particle enters the system in a new partition, and is a selectable parameter that controls the tendency of the ensemble to settle into larger vs. smaller numbers of partitions. The openness of the grand canonical ensemble means that particles (data vectors) can enter or leave the ensemble, and in particular can move from one partition to another. In this disclosure, the volume of the grand canonical ensemble can be treated as a constant, and can have no significance with respect to the biological samples. In contrast to a physics-based ensemble, not all characteristics of particles need be included in the pseudo-energy calculation, and characteristics (e.g. individual data vector components, or groups of components) can also be allowed to move between partitions. Characteristics that result in a low pseudo-energy can be accumulated in a partition, while characteristics that increase pseudo-energy can be moved to other partitions where their contribution lowers the overall system pseudo-energy. This results in identification of not only clusters of particles, but groups of characteristics that best classify the particles.

Individual: A test subject or patient. The individual can be a mammal or a non-mammal. In various embodiments, the individual is a mammal. A mammalian individual can be a human or non-human. In various embodiments, the individual is a human. A healthy or normal individual is an individual in which a disease or condition of interest (including, for example, any type of cancer) is not detectable by diagnostic methods.

Inner Product: The inner product of two vectors A and B is a scalar denoted $\langle A, B \rangle$ or A·B. In general, the norm is defined with respect to a weighting function g, thus $\langle A, B \rangle = \Sigma_k g_k \cdot A_k \cdot B_k \|V\| = \Sigma_k g_k \cdot V_k \cdot V_k$, where the subscript k represents a component in the $k t^h$ dimension of the vector space. In some vector spaces, such as a Cartesian space, $g_k = 1$.

Metropolis criterion: The Metropolis criterion is applicable to a Monte Carlo procedure that seeks to optimize a parameter over many states of an ensemble. The random iterations of a Monte Carlo procedure can be accepted (i.e. the random iteration takes effect and is applied to the ensemble) or can be rejected (i.e. the ensemble remains in its prior state) according to the change in the parameter and the relative probabilities of the before-and-after states. According to the Metropolis criterion, if the random iteration causes a parameter change in the desired direction (e.g. lower pseudo-energy), then the random iteration is accepted, while if the parameter change is unfavorable, the probability of acceptance is the ratio PAFTER/PBEFORE, where the denominator and numerator are the probabilities of the before and after states of the ensemble respectively. In a thermodynamic model having temperature T, the probability of a state is exp(−E/kT), and the probability of acceptance is exp(−ΔE/kT) where ΔE is the change in energy due to the random iteration and k is the Boltzmann constant. In thermodynamic analog models, E can be a pseudo-energy, T can be a temperature parameter defined for the model, and k can be chosen so that kT has the same units as the pseudo-energy. A Monte Carlo procedure which seeks to optimize a parameter according to a Metropolis criterion can be dubbed a Metropolis Monte Carlo procedure.

Monte Carlo Procedure: A computational method in which a sequence of random iterations is performed, wherein the random iterations are chosen to follow a pre-determined probability distribution. Monte Carlo procedures can be applied to both temporally evolving problems and time-independent problems.

Norm: The norm of a vector V, denoted $\|V\|$ is a non-negative scalar representing the length of the vector, and is equal to the square root of the inner product of a vector with itself. In general, the norm is defined with respect to a weighting function g, thus $\|V\| = \Sigma_k g_k \cdot V_k \cdot V_k$, where the subscript k denotes a component in the $k^{th}$ dimension of the vector space. In some vector spaces, such as a Cartesian space, $g_k \equiv 1$.

Normalization: Normalization refers to a process of balancing components (e.g. of a vector) in different dimensions. Normalization coefficients provide weights to the different dimensions when making multi-dimensional calculations (e.g. of norm, magnitude, inner product, similarity, or pseudo-energy) with one, two, or more vectors.

Optimization: Examples of the disclosed technology seek to cluster biological samples by optimizing a pseudo-energy or similarity measure among data vectors characterizing the biological samples. One of ordinary skill having benefit of this disclosure will appreciate that optimization refers to a computer-implemented procedure that can be implemented by evaluating a parameter for a plurality of configurations and selecting a configuration and/or parameter value from among the evaluated configurations according to a predetermined criterion. The predetermined criterion can be having a maximum or minimum value of the parameter from among the evaluated configurations, or an optimum value of the parameter according to another criterion, such as closest parameter to a target value. However, selection of a best parameter value is not a requirement; in examples, certain evaluated configurations can be excluded before identification of the optimum, for example for violating a constraint or lacking some desired feature.

In examples, an iterative improvement procedure can be an optimization procedure, or a stochastic procedure such as a Monte Carlo procedure can be an optimization procedure. Furthermore, an optimization, improvement, or Monte Carlo procedure is not required to proceed monotonically toward improved parameter values; in examples, such a procedure can traverse and evaluate arbitrary ranges of configurations, including some with degraded parameter values, in any order, as part of determining a selected configuration and/or parameter value.

In this disclosure, the terms "optimization," "minimization," and "maximization" related terms refer to any procedure that attempts to find configurations of a system that have superior values of a parameter as compared with other configurations of the system.

Particularly, one of ordinary skill will appreciate that optimization requires neither perfection nor an infinite search. Due to discrete data representations and finite computation time, an optimization procedure can successfully terminate without finding an exact extremum. Further, an optimization procedure can select from among any number of evaluated configurations, even as few as two.

Pseudo-energy or any other quantity is said to be substantially optimized (minimized or maximized) when an optimization procedure reaches a successful termination condition. Successful termination conditions can be defined in terms of convergence (improvements in the evaluated parameter being below a predetermined threshold), in terms of a bound or target (the evaluated parameter is within a predetermined tolerance of the bound or threshold), in terms of the history of the procedure (newer parameter evaluations cannot improve upon an older evaluated parameter), or in other ways as are known in the art. Optimization procedures can be terminated once there is evidence of little or no change between available sampling configurations. This can be achieved either by monitoring the entropy of the state occurrence description vector; by many failed attempts to achieve new and better conformation above a threshold; or by detecting an oscillatory pattern in state displacement between convergent multimodal states.

Particle: In this description, a particle is a constituent of a grand canonical ensemble that is identified with a data vector of a biological sample.

Partition: In this description, a partition is a unit of organization of a grand canonical ensemble. An active partition is one in which particles (data vectors) interact, thereby contributing to the pseudo-energy of the partition and to the pseudo-energy of the ensemble as a whole. A null partition is one in which particles (data vectors) are non-interacting and do not contribute to any pseudo-energy. The null partition allows modeling of particles that have exited the grand canonical ensemble, yet can also be considered to be part of the grand canonical ensemble.

Pathway: A communication process governing cellular activity, action, and response to intra- and extra-cellular signaling factors.

Phase: A phase is a macroscopic state of a plurality of particles, which can be a state of matter or a magnetic phase for atomic or molecular particles in a conventional grand canonical ensemble, or which can be a cluster of particles in a partition in the grand canonical ensembles of this description.

Pseudo-distance: Particles in an active partition can be placed with an ordering. In some examples, the particles are placed in one-dimensional integer positions, and the pseudo-distance between particles can be simply the difference between the two integer positions as a dimensionless positive integer number. In other examples, multi-dimensional positions or continuous positions can be used, and any of a variety of distance metrics (e.g. Cartesian, Manhattan, Chebyshev) can be used.

Pseudo-energy: Pseudo-energy is a quantity defined in a thermodynamic analog system to play the role of an energy in an analogous thermodynamic system. In this disclosure, pseudo-energy is defined on particles representing biological sample data vectors and on partitions of a grand canonical ensemble. Pseudo-energy can be defined for two particles, for a group of more than two partitions, for all particles in a partition, for a group of partitions of the ensemble, or for the entire ensemble. For particles, pseudo-energy can be taken as an inverse measure of similarity between the particles, so that lower pseudo-energy corresponds to increasing similarity, and minimization of ensemble or partition pseudo-energies corresponds to clustering of similar particles (data vectors). However, this is not a requirement, and pseudo-energy could be defined to increase with similarity so that the optimization procedures described herein seek to maximize pseudo-energy. One of ordinary skill will appreciate that the sense of positive or negative pseudo-energy is arbitrary, and that the descriptions, throughout this disclosure, of minimizing pseudo-energy also encompass alternative models where clustering is achieved by maximizing pseudo-energy: maximization of a first pseudo-energy $E_1$ equivalent to minimization of a second pseudo-energy such as $-E_1$. Pseudo-energy can include index weighting and distance weighting as described herein. For partitions and ensembles, pseudo-energy can include a sum of pairwise particle pseudo-energies; additional terms can also contribute.

Random: A random quantity is one whose value cannot be predicted precisely, although it can have a well-defined probability distribution. Particularly, random quantities are independent; the value of a first random quantity has no effect on the probability distribution of the second random quantity. In practice, one of a number of hardware-based or software-based techniques can be used to generate random quantities that can be pseudo-random rather than truly random; such pseudo-random quantities are included within the scope of "random" and related words in this disclosure. A random process is sometimes called a stochastic process, and can be a Monte Carlo process.

Sequence Read: A sequence of contiguous base pairs of a nucleic acid molecule. The sequence read may be represented symbolically by the base pair sequence (in ATCG) of the sample portion. It may be stored in a memory device and processed as appropriate to determine whether it matches a reference sequence or meets other criteria. A sequence read may be obtained directly from a sequencing apparatus or indirectly from stored sequence information concerning a sample.

Similarity: Similarity is a quantitative measure indicating the degree of likeness between two or more samples, objects, or data vectors. A similarity score, a cosine similarity function, correlation metric, or another measure can be used. Similarity measures can incorporate weighting to balance the relative importance or scaling of different attributes or components of data vectors. Weighting can also be dependent on the value of a component or attribute; for example, two vectors sharing a True or Present attribute may receive a greater contribution to similarity for that attribute than if the two vectors shared a False or Absent attribute. In other words, some attribute states can be uninteresting from the point of view of similarity; a shared uninteresting attribute can even contribute zero to the vectors' similarity. Generally, similarity increases with degree of likeness, and a vector can have higher similarity to itself than to any vector distinct from itself.

In this disclosure, pseudo-energy can be associated with an inverse similarity, which can be any function that is monotonically negatively correlated with the similarity. For example, inverse similarity can be the negative of the similarity or the reciprocal of the similarity, together with any suitable additive or multiplicative constants or functions.

Simulated Annealing: Simulated annealing is a technique for combining coarse or broad search across a wide search space with fine resolution search in the vicinity of a desired optimum. Simulated annealing, sometimes dubbed simply annealing, can be used in conjunction with a Metropolis Monte Carlo procedure in which a temperature is used to control the vigor with which the space is searched: at high temperatures, large jumps across search space are favored, while at low temperatures small movement across a narrow search space are favored. Thus, the annealing technique starts with a high temperature for coarse search across a wide search space, and gradually lowers the temperature so that the modeled system homes in on a particular optimum point in the search space. In examples, the temperature can be varied cyclically in a pattern, to perform multiple annealing cycles.

Data Vector: A data vector is a finite ordered collection of numerical quantities. A vector having N components is dubbed an N-dimensional vector and has a magnitude and direction in an N-dimensional space dubbed the vector space, except that no direction is defined for a vector having zero magnitude. The magnitude of the vector is its norm.

One of ordinary skill will recognize that the use of a vector in this disclosure can offer convenient conceptualization but is not a requirement. The vectors described herein could equivalently be cast in terms of other data structures, singly or in combination, including without limitation arrays, graphs, hashes, lists, tables, or trees, all of which are included within the scope of the disclosed technologies.

II. Overview

In brief, the technology described herein applies optimization methods to a grand canonical ensemble to find clusters of biological samples having maximized similarity in a biological and/or genetic space. The biological samples are modeled as particles of the grand canonical ensemble; gene measurements, together with other measurements or observable attributes, can play the role of coordinates; and a measure of inverse similarity, dubbed a pseudo-energy, plays the role of interaction energy between the particles. The particles can be variably distributed among partitions of the grand canonical ensemble in a manner analogous to physical particles such as atoms and molecules being distributed among solid, liquid, and gas phases of a conventional grand canonical ensemble with varying interaction energies in each phase.

Some of the operations that can be applied to a grand canonical ensemble of biological samples include: randomized Monte Carlo operations with both intra-partition and inter-partition exchanges of particles; a Metropolis criterion for accepting randomized operations according to energy difference or state probability, to drive the grand canonical ensemble toward a pseudo-energy minimum; deterministic operations analogous to evolution of a molecular dynamics (MD) system; iterative random and/or deterministic operations to explore the available configuration space of the grand canonical ensemble; and simulated annealing to balance coarse and fine exploration.

Through the disclosed improvement or optimization procedures, the grand canonical ensemble can converge to a configuration in which the pseudo-energy is minimized in every partition, which is equivalent to finding clusters of maximally similar biological samples. The disclosed technology can provide well-characterized cell clusters in a complex sampling of many cells, even when the population is grossly underdetermined, with many fewer samples than dimensions. In some examples, the clusters can be distinct, while in other examples the clusters can overlap. With the disclosed technology, clustering of high-dimensional vectors can be performed without recourse to ad hoc or empirical dimensionality reduction. No mathematical models need be used in contravention of their fundamental assumptions. The method requires no a priori assumptions about the nature and distributions of the observables. The disclosed technology can address clustering and classification problems that are out of reach of conventional technology.

Once determined, clusters can be used to identify feature sets of interest (such as gene expression patterns, mutation patterns, gene expression signatures, or mutation signatures) that are correlated with disease states or other observables. The feature sets can be used to identify characteristic genes and pathways for one or more of the clusters, which discriminate between clusters and can be used as classifiers for additional biological samples (e.g. cells).

Specifically, the disclosed technology can be used to identify potential quality attributes for cell-based therapies by applying it to single-cell mRNAseq and qPCR measurements, or other types of single cell cytometric data (e.g., morphologic features, protein expression, protein phosphorylation, DNA or histone modification, chromatin accessibility, etc.). Studies can be done on various cell types, including bone marrow stromal cells and engineered retinal pigment epithelial cells. Further, the method can be used for evaluation of any category of cell therapy product to identify therapeutically important cell types, allowing for improved manufacturing and testing of cell therapy products and more accurate dosing of these products. The method can inform strategies to enrich cell therapy products with desirable cells or to deplete undesirable cells in cell therapy products.

Because attributes of a biological sample can form part of a medical record, the technology can be naturally extended to medical records, another high dimensional space. Classifiers can be determined for patients experiencing rare adverse events, or prognostic factors can be identified for favorable or unfavorable disease outcomes.

Additionally, the disclosed technology can serve to discover physiologic attractor states of cells or disease conditions where seemingly heterogeneous states might have underlying physiologic or evolutionary conditions that are under bistable control (for example, diagnostic subcategories of prostate cancer, which can vary from indolent to highly aggressive, with major implications as to therapy). Hidden correlations can be uncovered. Hysteresis (biological memory) between cell states can be studied, in order to discover long term cell and disease conditions. This can be of particular value to understand and treat disease evolution where multiple correlating factors have a complex interaction over different characteristic time frames, or to help guide design of processes for manufacture of cell therapies.

Beyond development of cell-based therapeutics, the disclosed technology can address a need on the regulatory side, for example to identify quality attributes for cell-based products. Subgroups of subjects in multifactorial epidemiologic data sets can be determined. Quality attributes can also be found by applying the method to large scale high-throughput sequencing data sets. These attributes can then be used to select sets of analytical tests for monitoring the manufacturing process as well as for quality assurance of the final product. For example, identification of Quality Attributes—characteristics of a pharmaceutical product that can be used to develop specifications that ensure safety and effectiveness—has been a formidable challenge to the development of novel cell-based therapies. The method described would allow implementation of specifications as described by international consensus (see ICH Topic Q6B Specifications: Test Procedures and Acceptance Criteria for Biotechnological/Biological Products, available at http://www.ema.europa.eu/docs/en_GB/document_library/Scientific_guideline/2009/09/WC500002824.pdf/).

Furthermore, certain examples of the disclosed subject matter provide an improvement to computer performance in, for example, forming clusters of biological samples and/or extracting biological cluster features. In certain examples, adequate solutions to previously intractable problems can be provided, and provided more efficiently, than previous attempts. For example, clustering problems on vectors of about $10^6$ up to about $10^9$ dimensions could not be solved by conventional technology (for reasons such as numerical instability), and even if they could be solved, would suffer from infeasible computation times. Whereas, with the disclosed technology, such problems can be solved readily in reasonable time, and even multiple runs of an optimization or improvement procedure can be performed. As an example, the disclosed technology can efficiently use Boolean variables for many cell attributes that are observed to be bimodal in nature, and readily handles the sparse and statistically ill-characterized nature of such variables.

The Grand Canonical Ensemble supports multiple partitions, which, like phases of physical materials, can be organized to contain like particles within respective partitions. By suitable definition of a pseudo-energy function, organizing particles to increase or maximize similarity can be implemented by operations that attempt to find pseudo-energy reducing or pseudo-energy minimizing configurations of the partitions of particles.

Furthermore, the representation of particles by data vectors allows for efficient swap and other single-particle, two-particle, single-component, or two-component operations, which operate in an altogether different way than conventional clustering algorithms such as K-means, make no statistical assumptions about data vector components, and are immune to issues of high-dimensionality and the breakdown of distance and density metrics on which other conventional clustering algorithms depend.

Generally, the disclosed technology addresses a growing need for classification and clustering methods in ill-defined and very high dimensional spaces, of which NGS data is but one example.

III. Example Method for Classifying Biological Samples

FIG. 1 is a flowchart 100 depicting an example method for classifying a set of biological samples, denoted {S}, using a Grand Canonical ensemble of particles representing data attributes of respective samples, according to disclosed technology. Biological sample data can be obtained by NGS, by other techniques, and/or from other sources, as disclosed herein. The results of classification can be used to determine features and pathways of biological processes and medical treatments, and can lead to development of CBT.

At process block 110, a plurality of data vectors, denoted {V}, is formed. Each data vector V characterizes a respective biological sample S, which can be a single cell of an individual or a cell from a cell line or another source. Each data vector has a plurality of components, as many as on the order of $10^5$, $10^6$, up to on the order of $10^9$, or even higher. Each component can represent a measurement or other attribute of the biological sample. Some components can be obtained via single cell mRNAseq or ATACseq, NGS, or another high-dimensional cytometric technique.

At process block 120, one or more measures are defined, indicating similarity between two or more data vectors. As disclosed herein, different similarity and pseudo-energy measures can be used (e.g. using cosine similarity, Jaccard similarity, or a correlation metric). As a matter of convention, pseudo-energy can be defined such that greater similarity corresponds to lower energy, but this is not a requirement. A pseudo-energy measure can be defined on a pair of data vectors. A pseudo-energy measure can also be defined on a partition containing multiple data vectors. A partition pseudo-energy measure can include a sum of pairwise pseudo-energies for each possible data vector pair, and can include additional terms for the partition as a whole. A pseudo-energy measure can be defined for an ensemble of multiple partitions. The ensemble pseudo-energy can include a sum of partition pseudo-energies, and can also include additional terms reflecting pairwise interactions between partitions or for other purposes described herein.

At process block 130, a grand canonical ensemble model is configured and optimized or improved. Each particle of the grand canonical ensemble model corresponds to a respective data vector of a biological sample. The particles are organized into active partitions which can represent phases of the grand canonical ensemble. Additionally, a null partition can be implemented to store non-interacting particles, thereby modeling the openness of a grand canonical ensemble. Process block 130 operates to optimize or improve one or more of the similarity measures by an iterative procedure. In examples, particles are redistributed among partitions in such a way as to minimize one or more pseudo-energy measures; the number of partitions can vary dynamically; different pseudo-energy measures can be used in different partitions; particles can be cloned into multiple partitions; and/or vector components can be shuffled among partitions. However, none of these are requirements. Example grand canonical ensembles can be optimized with a fixed number of partitions; active partitions can have identical pseudo-energy measures; particles can be unique, meaning that a single biological sample can be represented in at most one partition; and/or data vector components can be identical in all partitions.

Through iterative improvement, the similarity measures are increased. In examples, the optimization or improvement procedure arrives at a distribution of particles among active partitions that decreases one or more pseudo-energy measures or, equivalently, increases similarity. In varying examples, pseudo-energy measures can be minimized independently for all active partitions, pseudo-energy measures can be minimized in one or more but not all active partitions, or an ensemble pseudo-energy measure can be optimized over all active partitions Minimization of ensemble pseudo-energy can be found with concurrent minimization of partition pseudo-energy for zero, one, some, or all of the active partitions Minimization of pseudo-energy is equivalent to maximization of similarity between data vectors in one or more partitions.

At process block 140, a set of selected partitions, denoted {P}, is determined at the point of reduced or minimized pseudo-energy. Each selected partition P contains a set of particles having associated data vectors of a corresponding set of biological samples. Through the operation of the optimization process, this set of biological samples has a maximized similarity, and is a cluster of biological samples. Thus the set of selected partitions {P} leads to classification or clustering of the biological samples {S} into respective subpopulations.

The description of flowchart 100 above encompasses numerous variants. With this disclosure in hand, one of ordinary skill will appreciate that many additional variations are possible within the scope of disclosed technologies, as described herein.

Figure 2:
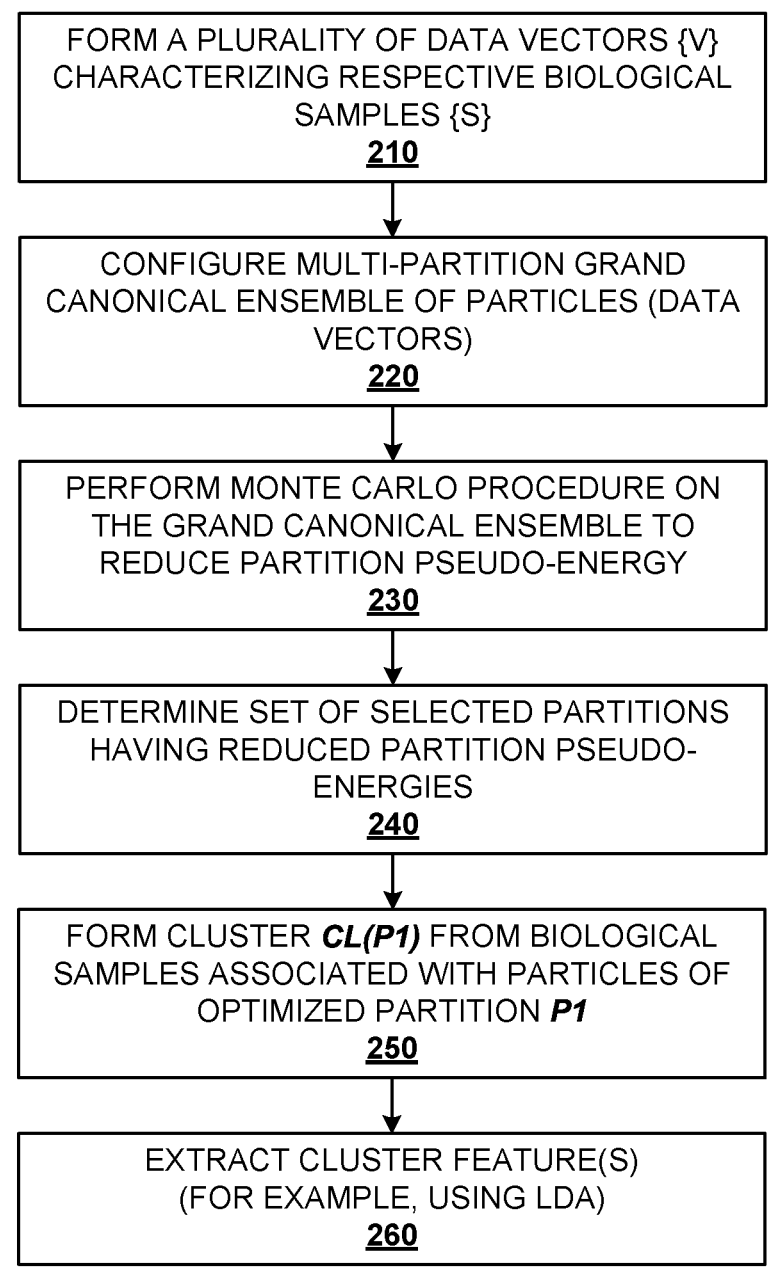
FIG. 2 is a flowchart depicting an example method for clustering biological samples and extracting cluster features, using a Grand Canonical ensemble of particles representing data attributes of respective samples, according to disclosed technology.

IV. Example Method for Clustering Biological Samples and Extracting Cluster Features FIG. 2 is a flowchart depicting an example method for clustering biological samples and extracting cluster features, using a Grand Canonical ensemble of particles representing data attributes of respective samples, according to disclosed technology. Biological sample data can be obtained by NGS or other techniques. The clustering results can be used to determine features associated with pathways of biological processes and medical treatments, and can lead to development of CBT.

At process block 210, a plurality of data vectors, denoted IV), is formed. Each data vector V characterizes a respective biological sample S, which can be a single cell of an individual or any other biological specimen or clinical subject data. Each component can represent a measurement or other attribute of the biological sample. Some components can be obtained via mRNAseq or another technique.

At process block 220, a multi-partition grand canonical ensemble model is configured. A multi-partition grand canonical ensemble model supports zero, one, or more partitions; in examples the number of partitions can vary dynamically. Each particle of the grand canonical ensemble model corresponds to a respective data vector of a biological sample. The particles can be moved within a single partition or between partitions. The multi-partition grand canonical ensemble can be initialized with zero partitions, one active partition (in which particles interact), one null partition (in which particles are non-interacting), or with multiple partitions.

At process block 230, a Monte Carlo or other stochastic procedure is performed on the multi-particle grand canonical ensemble model to reduce partition pseudo-energy of one or more partitions. The Monte Carlo procedure operates by redistributing the particles among the partitions, which can include moving particles to or from a non-interacting null partition. Reduced pseudo-energy corresponds to increased similarity of the particles within a given partition.

At process block 240, responsive to successful termination of the Monte Carlo procedure, the resulting partitions of particles are determined to be a set of selected partitions, which in examples can be a set of optimized or improved partitions, having reduced pseudo-energy, collectively or individually, as sought.

At process block 250, the particles in a first selected partition P1 are mapped back to their biological samples to form a first cluster CL(P1) of biological samples. In examples, some or all of the selected partitions {P} are mapped to respective clusters of the biological samples. In varying examples, a partition resulting from the Monte Carlo procedure can be empty, every selected partition can have at least one, two, or a predetermined minimum number of particles, a biological sample can remain unassigned, or every biological sample can be assigned to exactly one selected partition.

Then, at process block 260, any one of several methods is used to operate on the characteristic sets or data vectors of the first cluster to extract cluster features, which can be used to distinguish it from other clusters. In examples, feature extraction can be performed by linear discriminant analysis (LDA), support vector machines (SVM), or another naïve comparison technique.

With this disclosure in hand, one of ordinary skill will appreciate that many additional variations of flowchart 200 are possible within the scope of disclosed technologies. For example, other stochastic or deterministic procedures can be used in addition to, or alternative to, the Monte Carlo procedure.

V. Example Data Flow Using Grand Canonical Ensemble for CBT Development

Figure 3:
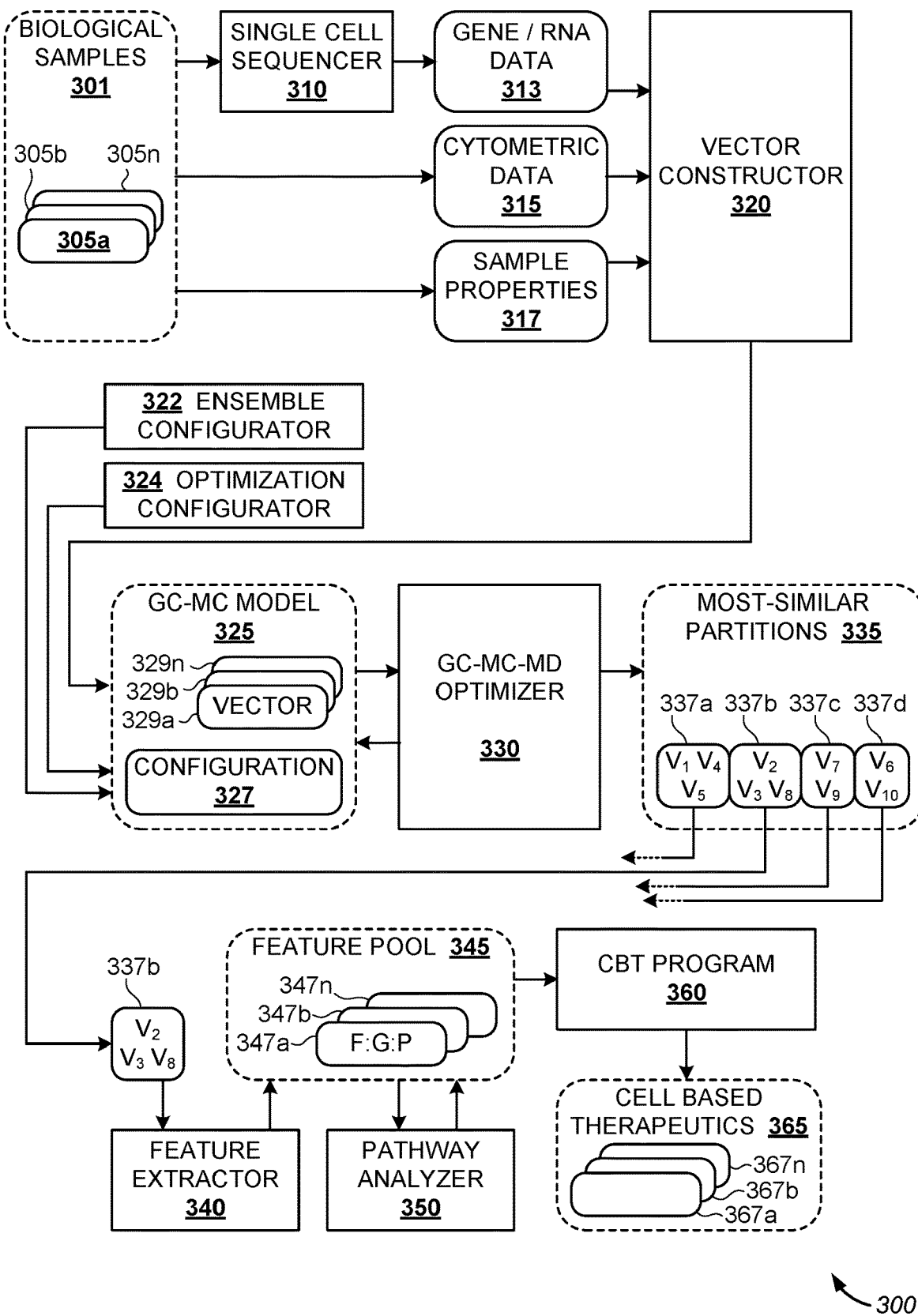
FIG. 3 is a data flow diagram illustrating an exemplary process for applying Grand Canonical-Monte Carlo procedure on biological samples to characterize cell-based therapeutics (CBT), a necessary step in their development, according to disclosed technology. A front-end process prepares data vectors representing respective biological samples. A central process prepares a Grand Canonical ensemble model from these data vectors and applies an optimization procedure to determine clusters of samples having maximized similarity. A back-end process extracts features from a cluster of samples, identifies relevant genes and pathways, which are used to develop and evaluate cell-based therapeutics.

FIG. 3 is a data flow diagram 300 illustrating an exemplary process for applying Grand Canonical-Monte Carlo procedure on biological samples to facilitate development of cell-based therapeutics (CBT), according to disclosed technology. In diagram 300, procedures and software modules are shown in square-cornered rectangles, while data objects and aggregates of data objects are shown in rectangles with rounded corners. The data objects can be input to, output from, or operated on by associated procedures or software modules.

In the top row of diagram 300, a front end process prepares data vectors representing respective biological samples. A set of biological samples 301 includes individual samples 305a-305n. Gene and/or RNA data 313, such as a genome sequence or an mRNA transcriptome, can be obtained by single-cell mRNA sequencing (scmRNAseq) 310, using NGS, or by another technique. Other cytometric data 315 can be obtained, such as morphological features or protein phosphorylation data, using corresponding techniques (not shown). Finally, other sample properties 317 may be known from medical or other records associated with the biological sample, such as a disease state, age, treatment history, dietary or lifestyle factors, or other individual characteristics of interest. Vector constructor 320 utilizes gene/RNA data 313, cytometric data 315, and sample properties 317 to construct a respective data vector for each biological sample 305a-305n. Each data vector may have a virtually unlimited number of components (limited only by the amount of computer memory available) representing various information items contained within data 313, 315, 317. Data vectors can also incorporate metadata, such as indications of the source of the sample or the source of NGS or cytometric data, which can be valuable for quality control, including detection of artifacts. Collectively, the components of a data vector characterize a biological sample.

In examples, vector components can be any mix of binary or Boolean values, values from a coded set, integer values, or continuous values; vector components can be scaled by a multiplier, an offset, a linear transformation, or a nonlinear transformation. Examples of binary or Boolean values can include gender, presence/absence of a particular gene expression, effectiveness or ineffectiveness in a preclinical or clinical study, or presence/absence of a particular disease state. Examples of coded sets can include blood type (e.g. A, B, AB, O) or a DNA mutation at a particular site (e.g. no mutation, base change C, base change G, base change T, insertion, or deletion). Examples of integer variables can include a number of chemotherapy treatments, a number of family members afflicted by a disease, or discretized representations of continuous variables such as age. Examples of continuous variables can include concentrations of enzymes or peptides, bone density, or an individual's weight.

The middle row of diagram 300 depicts a central process in which a Grand Canonical ensemble model 325 is prepared from the aforementioned data vectors and an improvement or optimization procedure is performed on the model to determine clusters of samples having maximized similarity. Ensemble configurator 322 is a module that defines the configuration of the Grand Canonical ensemble, including for example pseudo-energy functions, weighting functions, and parameters controlling pseudo-spatial ordering of particles within a partition, whether particles can be replicated in multiple partitions, whether the number of partitions is fixed or variable, whether and which data vectors can be shuffled, and other parameters. Optimization configurator 324 is a module that defines the configuration of the optimization process, including for example the specific random or deterministic operations that can be performed, the control of simulated annealing or temperature cycling, conditions for determining energy minima at which selected partitions can be recorded, the control of reset, restart, or continuation of the optimization process after one or more pseudo-energy minima have been attained, and other operational controls. Together, the optimization configuration and ensemble configuration are stored in configuration repository 327. The Grand Canonical ensemble model 325 also includes the data vectors 329a, 329b-329n that correspond respectively to samples 305a, 305b-305n. In examples, model 325 is configured to be optimized using random operations according to a Monte Carlo procedure, optionally including a Metropolis criterion for accepting or rejecting Monte Carlo swap operations, and can be labeled a Grand Canonical-Monte Carlo model, or GC-MC model for short. However, the use of a Monte Carlo procedure is not a requirement of the disclosed technologies.

Optimizer 330 operates on the grand canonical model 325 using one or more types of operations such as intra-partition Monte Carlo operations, intra-partition deterministic operations, or inter-partition grand canonical operations.

Intra-particle Monte Carlo operations can be swaps of two randomly selected particles or swaps of two randomly selected data vector components. Such an operation can be accepted automatically if it results in a lowering of partition pseudo-energy. In examples, if the operation would result in an increase of partition pseudo-energy, then it can be randomly accepted with a probability proportional to $\exp(-\Delta E/kT)$, where $\Delta E$ is the increase in partition pseudo-energy, T is a pseudo-temperature variable in the optimization procedure, and k is a configurable constant analogous to the Boltzmann constant in thermodynamics. Effectively, kT can be viewed as the optimization temperature measured in the same units as the pseudo-energy.

Intra-partition deterministic operations are evolution steps driven by energy differentials. Two neighboring particles can be swapped if the swap results in a lowering of particle pseudo-energy. In examples, neighboring components of the data vectors can have their indices exchanged if the swap results in a lowering of particle pseudo-energy. In examples, the deterministic operation operates on all neighboring pairs of particles and/or neighboring data vector components. The deterministic operations can be implemented sequentially, comparing positions 1 and 2, then 2 and 3, then 3 and 4, and so on. Alternatively, the deterministic operations can be vectorized by comparing 1 and 2 at the same time as 3 and 4, 5 and 6, and so on, followed by a comparison of positions 2 and 3, 4 and 5, and so on.

Inter-partition grand canonical operations are movements of particles and/or vector components among partitions. Particles can move from one active partition to another. Particles can move from a null partition to an active partition or vice versa. In examples, particles can be replicated from one partition to another, or can be deleted from an active partition. In examples, similar operations can be performed on components of the data vectors, such that for a given particle, one set of data vector components are present in a first active partition, while a disjoint second set of data vector components are present in a second partition which can be another active partition or a null partition. Particles moving between partitions are analogous to phase transitions in an ensemble of physical particles. Particles moving between an active partition and a null partition are equivalent to particles entering or leaving the grand canonical ensemble. Movements of data vector components can be generalizations of particle movements. Any of these operations can be used in varying combinations as part of an improvement procedure directed to minimization of one or more pseudo-energy measures.

Through optimization or improvement, a set 335 of selected partitions is obtained, containing example partitions 337a-337d. The selected partitions correspond to minimization of one or more pseudo-energy measures and accordingly contain particles that are maximally similar according to the configured pseudo-energy measure. In the illustrated example, selected partition 337b contains particles having data vectors V2, V3, and V8. In examples, the complete set 335 is obtained at a single point in the optimization process, while in other examples, one or more selected partitions are determined as respective snapshots of a continuing optimization process. In further examples, multiple iterations of the optimization process can be performed on the grand canonical model 325 to acquire successive groups of one or more selected partitions. In some examples, each selected partition or group of selected partition can be assigned a score representing the quality or value of pseudo-energy minimization achieved. These scores can be used to select promising partitions for subsequent analysis.

In the bottom row of diagram 300, a back end process extracts features from a cluster of samples, identifies relevant genes and pathways, which are used to develop and evaluate cell-based therapeutics. As illustrated, partition 337b is selected for processing. One or more other selected partitions can be processed similarly. Feature extractor 330 determines common features of the cluster of biological samples represented by the particles of partition 337b. In examples, feature extraction can be performed using linear discriminant analysis (LDA) or other methods, with or without component weighting (based on permuted component indices) or pseudo-distance information included in partition 337b. As an illustration, features of partition 337b could be found to be a combination of a particular disease state, a particular expressed gene, and a concentration of a particular enzyme.

One or more features F of a selected partition can be accumulated in feature pool 345, which contains feature structures 347a-347c for each analyzed partition 337. Pathway analyzer 350 can operate on one or more of feature structures 347a-347c to determine relevant genes G and possible pathways PW which can be accumulated into the feature structures 347a-347c. The identified features F, genes G, and/or pathways PW can be used as inputs to a program for CBT development and evaluation, leading to a set 365 of CBTs 367a-367c.

By determining features, the data flow of diagram 300 can lead to classifiers for biological samples. As candidate CBTs are identified, a similar data flow can be performed on biological samples treated with each candidate CBT to detect, for example, a correlation between the candidate CBT and a disease state, thereby providing an evaluation of the candidate CBT. The correlation can indicate a therapeutic effect or a desired biological effect.

The description of diagram 300 above encompasses numerous variants. With this disclosure in hand, one of ordinary skill will appreciate that many additional variations are possible within the scope of disclosed technologies, as described herein.

VI. Example Method for Optimization of a Grand Canonical Ensemble

Figure 4:
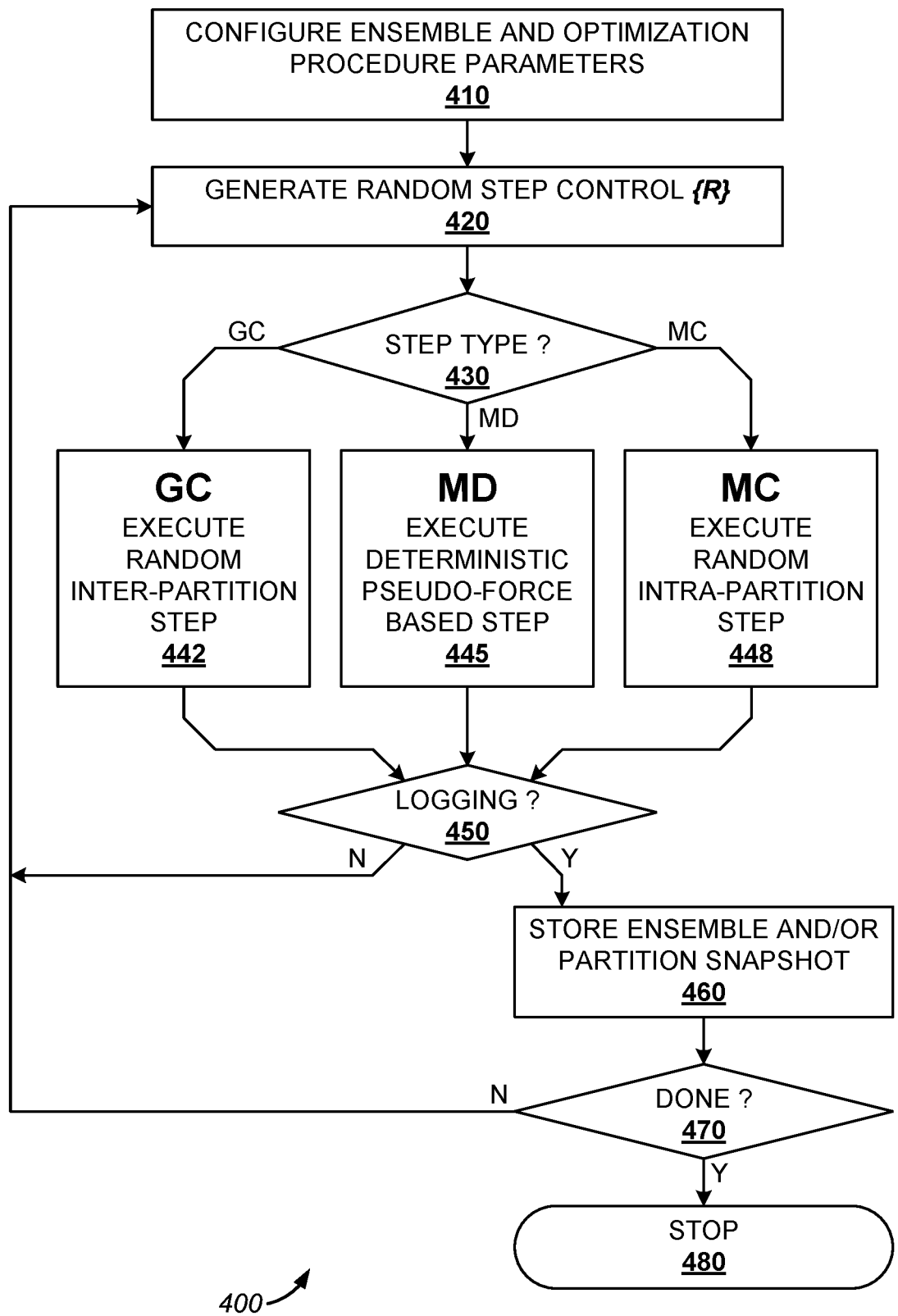
FIG. 4 is a flowchart of a stochastic procedure for performing an optimization procedure on a Grand Canonical ensemble according to disclosed technology.

FIG. 4 is a flowchart 400 of a stochastic procedure for performing improvement or optimization on a Grand Canonical ensemble according to disclosed technology. The method performs operations in a loop; different types of operations can be mixed in various ways.

At process block 410, a grand canonical ensemble is configured, and parameters controlling the optimization method are also configured. The grand canonical ensemble includes particles described by data vectors of respective biological samples, as described herein. Process blocks 420-450 or 420-470 describe the core loop of the optimization procedure.

At process block 420, a control is generated for an operation. In examples, all operations are random, for example according to a Monte Carlo procedure, and some operations can require the use of multiple random numbers. One random number can be used to select a type of operation according to a predetermined probability distribution, other random numbers can be used to select one or two partitions, one or two particles within the selected partition(s), one or two vector component indices, or other operation parameters according to the operation type, in any combination or sub-combination. Thus, process block 420 depicts a set of random numbers [R] used to randomly control an immediately following operation.

The optimization method can include a mix of randomized operations and deterministic operations, or even just deterministic operations. In examples where deterministic and randomized operations are mixed, the deterministic operations can be run according to a schedule (e.g. every tenth operation is a particular deterministic operation) or in response to a criterion being satisfied (e.g. performing one or more deterministic steps when a convergence criterion has been met). In such examples, no random number could be required or generated at process block 420 for the deterministic operation. In other examples, deterministic operations can be randomly incorporated into the operation loop (e.g. 7% of operations, at random, can be deterministic operations), in which case one random number is used at process block 420 to select a deterministic operation. In further examples, deterministic operations can incorporate random features (e.g. a deterministic operation is performed on one or more randomly selected partitions, rather than on all partitions).

At process block 430, an operation type is determined and the method branches accordingly.

If the operation type is GC, then the method follows the GC branch from process block 430 to process block 442, where a GC operation can be performed. A GC type of operation is a random operation in which content of one or more partitions is changed. In examples, this can include moving a particle from one partition to another, copying a particle from one partition into another partition, or deleting one among multiple copies of a particle. In examples, similar operations can be performed on vector components. A GC operation on a given particle can be regarded as a phase transition of the given particle.

If the operation type is MC, then the method follows the MC branch from process block 4 to process block 448, where an MC operation can be performed. An MC type of operation is a random operation within a partition, which can be performed according to a Monte Carlo procedure or according to another randomization technique. In examples, an MC operation can be a swap of two randomly selected particles within the partition. In examples, similar operations can be performed on vector components.

Randomized operations can include a mix of random and deterministic features. In some examples, a randomized operation can be operated according to a schedule (e.g. every third operation is a particle swap) with randomly selected features (e.g. which particles in which partition are to be swapped), while in other examples randomized operations can be formulated as a set of operations with fixed parameters, one of which is randomly selected.

Because the optimization method is directed to minimizing pseudo-energy measures, and a random operation could increase, decrease, or make no change to the pseudo-energy, not all randomized operations actually take effect. In some examples, a Metropolis criterion can be applied. Randomized operations that decrease pseudo-energy can take effect automatically, while randomized operations that increase pseudo-energy take effect with a probability that is a function of the pseudo-energy increase. An operation that does not take effect leaves the particles, partitions, and grand canonical ensemble in an unchanged configuration. In examples, if the operation would result in an increase of partition pseudo-energy $\Delta E$, then the probability of taking effect can be $\exp(-\Delta E/kT)$, where $\Delta E$ is the increase in partition pseudo-energy, T is a temperature variable in the optimization procedure, and k is a configurable constant analogous to the Boltzmann constant in thermodynamics Effectively, kT can be viewed as the optimization temperature measured in the same units as the pseudo-energy.

When T is small, even a small increase in pseudo-energy can have a vanishingly small probability of taking effect, which implies that the partition or ensemble is unlikely to jump away from a proximate local minimum. When T is large, only large increases in pseudo-energy are inhibited, which implies that the partition or ensemble is likely to jump away from a proximate local minimum, and could find a better minimum or even an absolute minimum of pseudo-energy. Gradual reduction of the temperature is sometimes described as simulated annealing and can be implemented as part of the loop control, for example at process block 420. Alternatively, the temperature can be cycled: as the temperature is lowered, the ensemble settles toward a particular minimum, which could be a local minimum of pseudo-energy. As the temperature is raised, the ensemble is more likely to move to another region of its state space, which can lead to another and possibly deeper minimum of pseudo-energy. In examples, different temperature profiles can be implemented, such as sinusoidal, triangular, or sawtooth shaped waveforms. Temperature can be controlled according to a schedule, or dynamically, for example according to the recent history of pseudo-energy. In some examples, the temperature can be uniform across the entire ensemble and all operations, while in other examples, each partition or operation type can have its own temperature or temperature control.

In some examples, process blocks 442 or 448 attempt to make a single operation, and the process block completes and proceeds to process block 450 regardless of whether the random operation takes effect. In other examples, a GC or MC operation that does not take effect causes the GC or MC operation to be retried, with different random parameters, within process block 442 or 448 until either an operation takes effect or a retry limit is reached.

Finally, if the operation type is MD, then the method follows the MD branch from process block 430 to process block 445, where an MD operation can be performed. An MD type of operation is a deterministic operation, and can be a dynamic evolution operation. In some examples, particle positions can be exchanged based on a pseudo-force, which is a gradient of pseudo-energy with respect to particle position. If exchange of two neighboring particles results in a decrease of pseudo-energy, then the particle positions are swapped. MD operations can be applied to all particles in all active partitions, or to a subset of partitions. In some examples, MD operations can include swapping of vector component indices according to a gradient of pseudo-energy with respect to component index. If exchange of two neighboring vector components results in a decrease of pseudo-energy, then the indices of these two vector components are exchanged. In some examples, a threshold can be applied: swaps are made only if the swap results in a pseudo-energy decrease greater than or at least equal to the threshold amount. In examples, the threshold amount can be zero.

When process block 442, 445, or 448 completes, the method proceeds to decision block 450, where a determination is made whether one or more partitions of the grand canonical ensemble model should be logged as selected partitions. A convergence criterion can be used to make this determination, for example, a change in pseudo-energy below a convergence limit within a predetermined number of preceding operations. In examples, the convergence criterion can be combined with other criteria, such as a global metric on the distribution of particles within partitions, or a plurality of pseudo-energy measures being simultaneously satisfied, or a requirement to have one or more post-convergence MD operations.

If the determination at process block 450 is not to perform logging, then the N branch is followed back to process block 420 for a next operation. If the determination is to log the state of one or more partitions, then the Y branch is followed to process block 460, where a snapshot of one or more partitions, or of the entire grand canonical ensemble, is stored. The method then continues to decision block 470, where a termination condition is checked. If the termination condition determines that the method has been completed, then the Y branch is followed to stop block 480, where the method terminates. However, if the termination condition has not been met, the N branch is followed, looping back to process block 420 for another operation. In examples, varying termination conditions can be used. Termination conditions can include requiring that every pseudo-energy measure be minimized at least once, that every partition be optimized, that a target number of selected partitions or ensemble snapshots be stored, or that a total amount of computation time has been exceeded. In examples, the method performs a single global minimization of the ensemble, so that process block 470 can be omitted and process block 460 leads directly to stop block 480. In examples, decision block 470 can be moved upstream of decision block 450, which allows for smooth termination of the method in the eventuality that the method fails to converge within a predetermined amount of computation time. In such examples, process block 460 can proceed directly back to process block 420. In examples, a predetermined or randomized reset of the ensemble configuration can be performed after each execution of process block 460.

The description of diagram 400 above encompasses numerous variants. With this disclosure in hand, one of ordinary skill will appreciate that many additional variations are possible within the scope of disclosed technologies, as described herein.

VII. Example Pseudo-Energy Weighting by Particle Pseudo-Distance

As described herein, pseudo-energies can be calculated between pairs of particles, and particles can be assigned to distinct positions (e.g. one-dimensional positions 0, 1, 2, 3, 4, . . . ; or . . . , −2, −1, 0, 1, 2, . . . ) within a partition. A pseudo-distance can be defined as the difference in position between two particles of a partition. Accordingly, when calculating pairwise pseudo-energies, a greater weight can be given to neighboring particles than to particles situated two, three, or more positions apart. In examples, pseudo-distance weighting can be a multiplicative factor, meaning that a similarity or pseudo-energy between two particles can be calculated initially without reference to the particle positions, which can be based on the respective data vector components, a weighting function for the components, and/or a weighting function dependent on component index. Then the initial calculation can be multiplied by the pseudo-distance weight according to the pseudo-distance between the two particles, to obtain a pairwise pseudo-energy for the two particles.

By way of illustration, in a partition with N particles, with $S_{ij}$ denoting the similarity between the data vectors of particles i, j, $d_{ij}$ denoting the pseudo-distance between these two particles, and W denoting the pseudo-distance weighting function, then the total particle pseudo-energy EP can be denoted as:

$$EP = \sum_{i=1}^{N-1} \sum_{j=i+1}^{N} W(d_{i,j}) S_{i,j}$$

FIGS. 5A-5F are graphs illustrating example dependencies of pseudo-energy weighting functions on distance between particles in a partition. In these illustrations, particle positions are assumed to take integer values in one dimension. Accordingly, pseudo-distance can take values 1, 2, 3, 4, . . . Pseudo-distance (labeled "distance") is plotted along the horizontal axis, and the pseudo-distance weight multiplier (labeled "weight") is plotted along the vertical axis. The axes are labeled in FIG. 5A; the other graphs FIGS. 5B-5F have similar axes. The weights can be negative values as shown, to reflect the fact that more positive similarity scores Sij correspond to attraction between the particles and a more negative pseudo-energy value, according to a sign convention for energy.

Figure 5A:
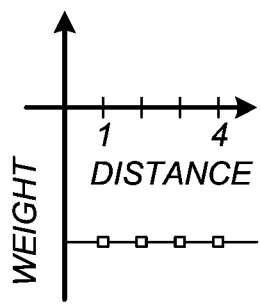
FIG. 5A-5F are graphs showing example dependencies of pseudo-energy weighting functions on distance between particles in a partition.

FIG. 5A is a graph for a uniform pseudo-distance weight, for which the weight of all particle pairs is the same, independent of distance: (d)=−1.

Figure 5B:
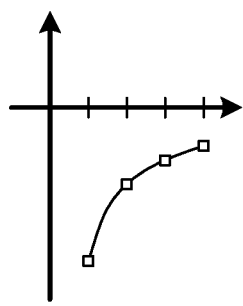

FIG. 5B is a graph depicting a pseudo-distance weight which is inversely proportional to pseudo-distance: $(d) \propto 1/d$.

Figure 5C:
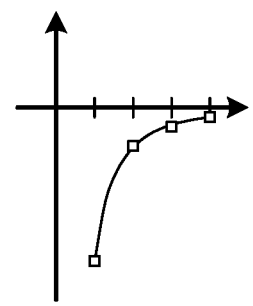

FIG. 5C is a graph depicting a pseudo-distance weight which is inversely proportional to the square of the pseudo-distance: $(d) \propto d^{-2}$.

Figure 5D:
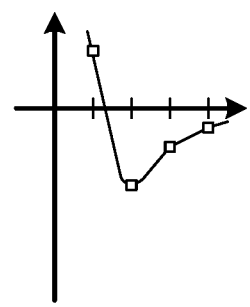

FIG. 5D is a graph depicting a pseudo-distance weight having competing attractive and repulsive terms, similar to a 6-9 Lennard-Jones potential:

$$W(d) \propto \left[ C1\left(\frac{d0}{d}\right)^9 - C2\left(\frac{d0}{a}\right)^6 \right],$$

where d0 is the pseudo-distance at which the weight function W is a minimum, and C1 and C2 are constants. When the ratio C1:C2 is 2:3, W(d) has an extremum at d=d0.

Figure 5E:
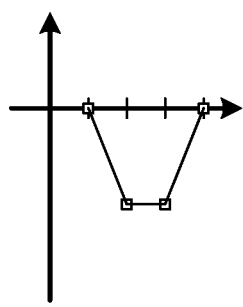

FIG. 5E is a graph depicting a pseudo-distance weight having a restricted range of attraction:

$$W(d) = \begin{cases} -1, & d \in [2, 3] \\ 0, & \text{otherwise} \end{cases}.$$

Figure 5F:
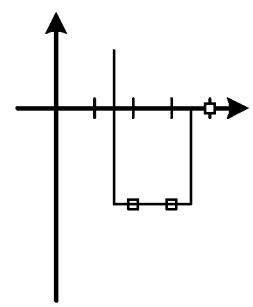

FIG. 5F is a graph depicting a pseudo-distance weight that approximates a Lennard-Jones potential:

$$W(d) = \begin{cases} 100, & d = 1 \\ -1, & d \in [2, 3] \\ 0, & d \geq 4 \end{cases}.$$

In some examples, all active partitions use the same pseudo-distance weight function, while in other examples the pseudo-distance weight function can vary between partitions.

As described above, FIGS. 5A-5F encompass numerous variants. With this disclosure in hand, one of ordinary skill will appreciate that many additional variations are possible within the scope of disclosed technologies.

VIII. Example Similarity Weighting by Component Index

As described herein, pseudo-energies can be calculated based on similarities between pairs of data vectors. Without weights, a simple example of a similarity score $S_{12}$ between two data vectors $V_1$, $V_2$ is the dot product, $$S_{12} = \Sigma_k V_{1k} \cdot V_{2k},$$

where suffix k denotes components of each vector. However, because the scaling and importance of each component can be different, component-wise normalization coefficients $g_k$ can be introduced:

$$S_{12} = \Sigma_k g_k \cdot V_{1k} \cdot V_{2k}.$$

Here, the normalization coefficient $g_k$ is defined for the attribute represented by each component. For example, a normalization coefficient of 1 can be used for vector components representing bimodal gene expressions, and a normalization coefficient of 0.1 can be used for vector components representing continuously variable enzyme concentrations.

Additionally, some examples of the disclosed technologies support variable index positions, allowing e.g. components at low index positions to be given more weight and components at high index positions to be less significant in a pseudo-energy calculation. Thus components {k} can be permuted: k ➤ $I_k$, and it can be advantageous to incorporate a weight function A that is dependent on the component index $I_k$. Such a weight function can be incorporated into the similarity calculation:

$$S_{12} = \Sigma_k A(I_k) \cdot g_k \cdot V_{1k} \cdot V_{2k}.$$

Figure 6A:
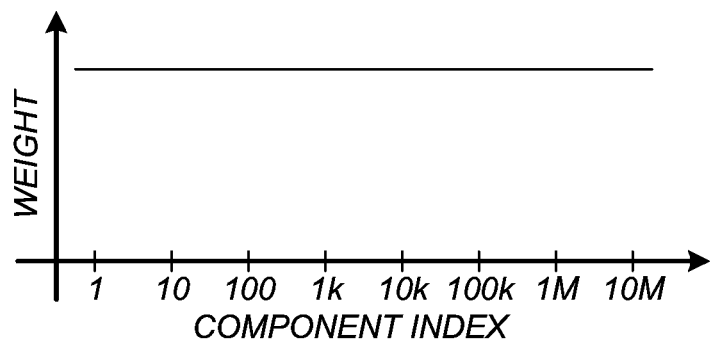
FIG. 6A-6C are graphs showing example dependencies of pseudo-energy weighting functions on component indices.
Figure 6B:
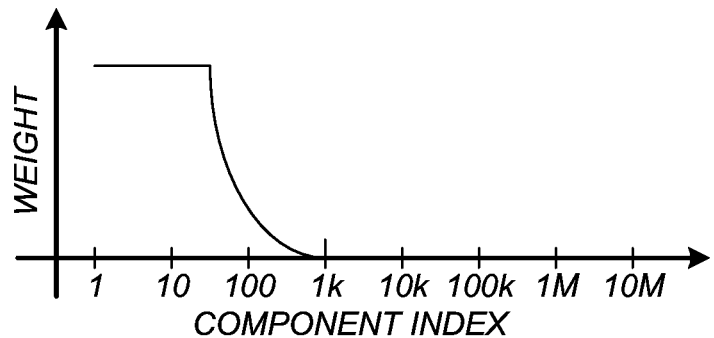
Figure 6C:
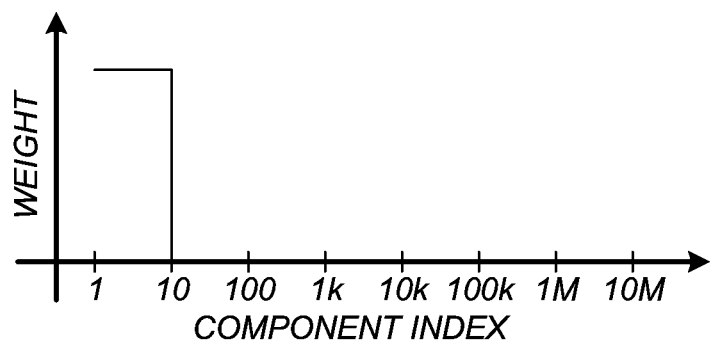

FIG. 6A-6C are graphs showing examples of index weighting functions. In these graphs, component index is represented on the horizontal axis using a logarithmic scale, from 1 to 10 million ("10M"). In varying examples, the number of components can be less or more than 10M. The index dependent similarity weight is plotted along the vertical axis.

FIG. 6A is a graph depicting a constant index weighting function, (I)=1. Such a weighting function can be employed in examples where component indices remain fixed.

FIG. 6B is a graph depicting an example segmented index weighting function:

$$A(I) = \begin{cases} 1, & I \leq 30 \\ \dfrac{30}{I}, & I > 30 \end{cases}.$$

In this example, a first segment of 30 index positions is assigned uniform weights, and a second segment of the remaining index positions is assigned progressively decreasing weights. Many variations are possible. The first segment can be any width, or can be eliminated. The second segment can employ any monotonically non-increasing function such as an exponential, a stair-step, or an inverse power-law.

FIG. 6C is a graph depicting an index weighting function having limited range: only the first ten index positions have any weight; the remaining index positions have weight zero and are ignored. Again, variations are possible.

In some examples, all active partitions use the same index weighting function, while in other examples the index weighting function can vary between partitions.

IX. Example Method for Calculating Pseudo-Energy of a Partition

Figure 7:
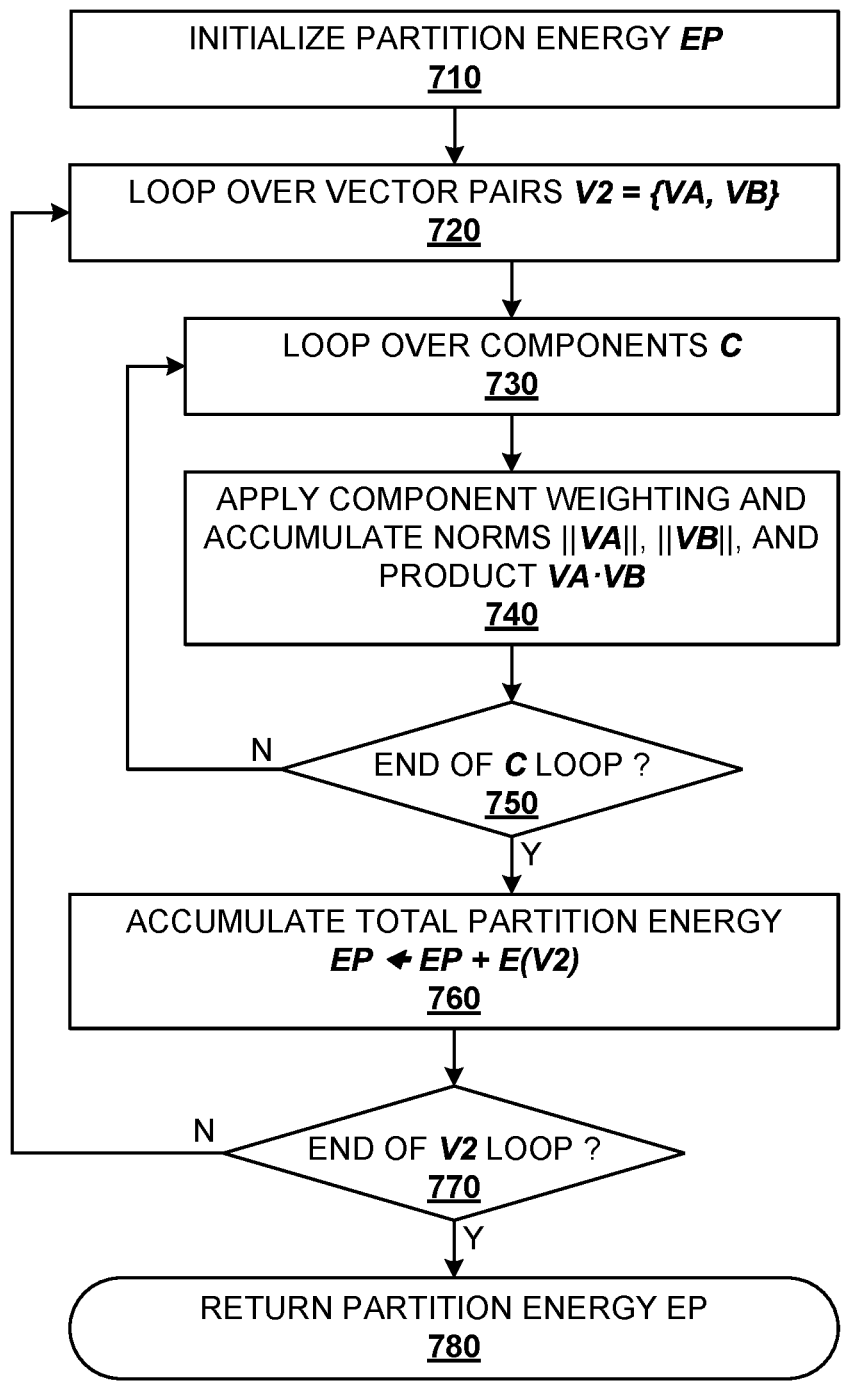
FIG. 7 is a flowchart of an example method for calculating pseudo-energy for particles in a partition, according to disclosed technology.

FIG. 7 is a flowchart 700 of an example method for calculating pseudo-energy for particles in a partition, according to disclosed technology. This method loops over pairs of particles; for each particle pair, an inner loop over components collects terms required to calculate similarity using cosine distance between the vectors. The similarity and then pseudo-energy are calculated for each particle pair; these pairwise energies are accumulated to obtain the total partition energy.

At process block 710, the partition energy EP is initialized. In some examples, the partition energy EP can be initialized to zero, while in other examples, the partition energy EP can be initialized to a non-zero value reflecting an energy cost of creating an additional partition. The latter case can serve to steer an optimization or improvement method away from configurations having large numbers of trivial partitions with just one or a few particles each.

At process block 720, a loop over particle pairs is begun. Each particle has an associated data vector; the pair of particles has two vectors VA, VB, which are collectively denoted V2. Although represented as a single block, one of ordinary skill will appreciate that the actions performed at process block 720 can differ between the first time through the loop and subsequent iterations. For example, on a first iteration, loop parameters can be initialized to begin the loop, while on subsequent iterations, loop parameters can be incremented or decremented, and other operations can be performed.

At process block 730, a loop over data vector components is begun. Besides initialization of the loop parameters, a first iteration of process block 730 can include initialization of terms accumulated on successive iterations of the loop. At process block 740, the contribution of the current component C to the norms of VA, VB and dot product VA·VB are determined and accumulated. In examples, these contributions can be $g_C \cdot VA_C \cdot VA_C$, $g_C \cdot VB_C \cdot VB_C$, and $g_C \cdot VA_C \cdot VB_C$ respectively, where $VA_C$ and $VB_C$ are the $C^{th}$ components of vectors VA and VB, and $g_C$ is the normalization coefficient for the $C^{th}$ component. In this illustration, normalization coefficients are used but index weighting is not. In other examples, index weighting could be incorporated into process block 740.

At decision block 750, a determination is made whether all components C have been considered. If not, then the N branch is followed back to process block 730 to continue with the next iteration of the C loop. If yes, then the calculations of norms and dot products are complete, according to:

$$\|VA\| = \sqrt{\sum_C g_C \cdot VA_C \cdot VA_C}$$

$$\|VB\| = \sqrt{\sum_C g_C \cdot VB_C \cdot VB_C}$$

$$VA \cdot VB = \sum_C g_C \cdot VA_C \cdot VB_C$$

Following completion of the C loop, the method follows the Y branch to process block 760. The cosine similarity and pseudo-energy can be calculated, $$S(V2) = \frac{VA \cdot VB}{\|VA\| \cdot \|VB\|}, \text{ and}$$

$$E(V2) = W(D(V2)) \cdot S(V2)$$

where D(V2) is the pseudo-distance between the current particle pair, and W is a pseudo-distance weighting function. Then, at process block 770, the pseudo-energy of the current particle pair is accumulated into the total partition energy.

At decision block 780, a determination is made whether all particle pairs have been considered. If not, then the N branch is followed back to process block 720 for the next iteration of the V2 loop. If yes, then the calculation of partition energy EP is complete. The partition energy EP can be stored or returned at process block 790, and the method can terminate.

Many variations are possible within the scope of disclosed technologies. For example, other similarity measures can be used, or the similarity measure can include an index weighting function, or a wide range of pseudo-distance weighting functions or no pseudo-distance weighting function can be used.

X. Example Method for Calculating Pseudo-Energy of the Ensemble

Figure 8:
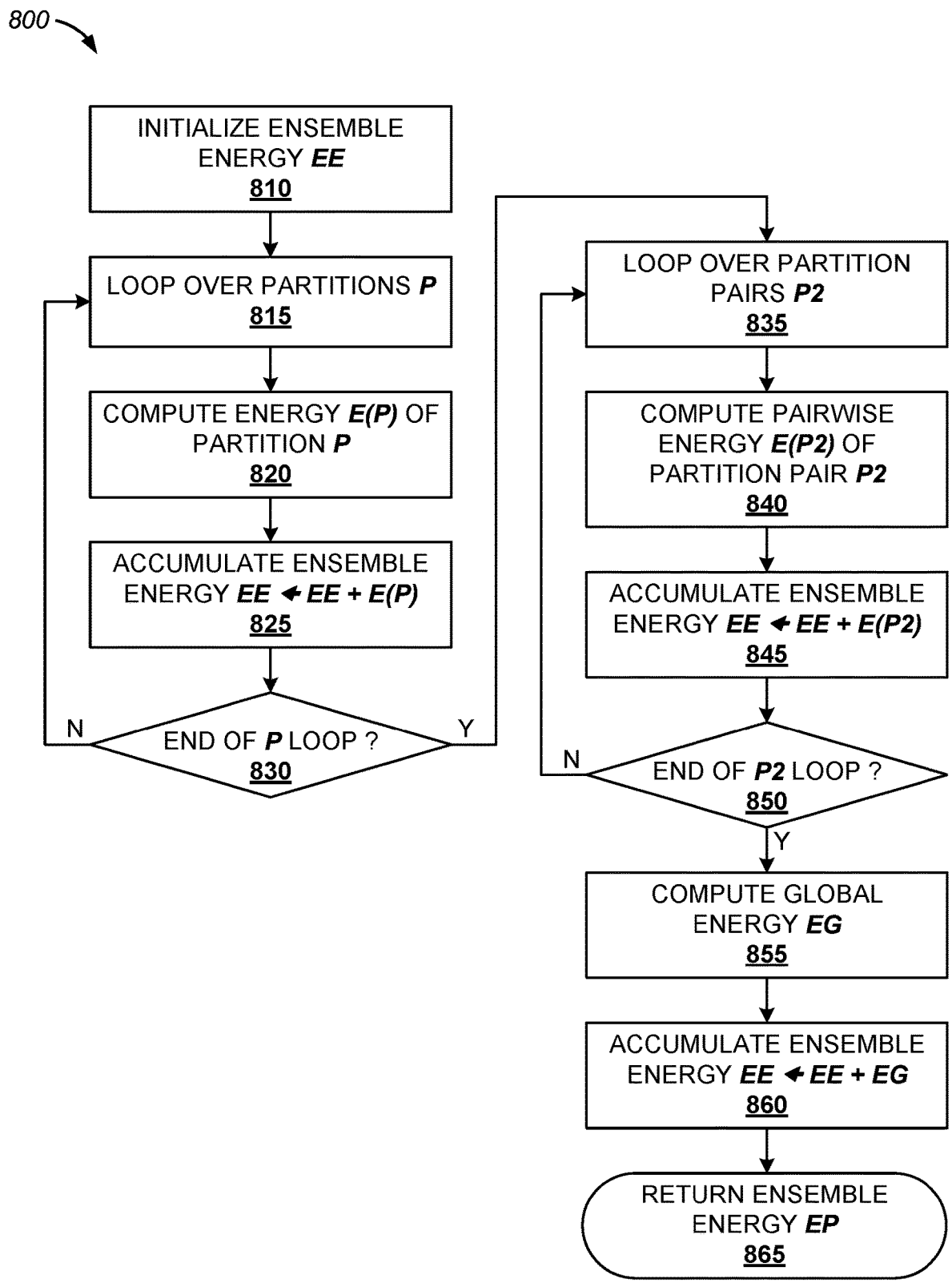
FIG. 8 is a flowchart of an example method for calculating pseudo-energy of a grand canonical ensemble, according to disclosed technology.

FIG. 8 is a flowchart 800 of an example method for calculating pseudo-energy of a grand canonical ensemble, according to disclosed technology. This method loops over partitions, determining and accumulating the partition pseudo-energies. Optionally, a second loop over partition pairs can incorporate pairwise interactions between partitions. Finally, optional global contributions to the pseudo-energy can be added into the ensemble energy.

At process block 810, the ensemble energy EE is initialized, for example to zero. At process block 815, a loop over partitions P is begun. As for other loops described in this disclosure, process block 815 can be understood to perform different operations on a first loop iteration, when loop parameters can be initialized, and on subsequent iterations, where loop parameters can be updated. At process block 820, the pseudo-energy E(P) of partition P is determined. In examples, a method described in the context of FIG. 7 can be used, or a similar method, or a different method. At process block 825, the energy E(P) is accumulated into the ensemble energy EE. At process block 830, a determination is made whether all partitions have been considered. If not, then the N branch is followed back to process block 815 for an iteration on the next partition. If yes, then the method follows the Y branch to process block 835.

Process blocks 835-850 perform a loop over pairs of partitions, to optionally calculate interaction pseudo-energies between partitions. Interaction pseudo-energies can be dependent on a degree of overlap or disjointness between the two partitions, or the numbers of particles in each partition, and can be used, for example, to steer the optimization towards disjoint selected partitions, or towards partitions having greater numbers of particles.

At process block 835, the loop over partition pairs P2 is begun. At process block 840, a pairwise pseudo-energy of a current partition pair P2 is determined, and at process block 845, the pseudo-energy E(P2) is accumulated into the ensemble energy EE. At process block 850, a determination is made whether the P2 loop is complete. If no, then the N branch is followed back to process block 835 to perform an iteration on the next partition pair. If yes, then the method follows the Y branch to process block 855.

At process block 855, optional global pseudo-energy terms EG can be calculated. Example global terms can be dependent on a number of partitions, a number of particles or vector components occurring only in a null partition, or any other measure that can be used to steer the ensemble optimization in a preferred direction or away from undesired extrema. At process block 860, the global energy terms EG are accumulated into the ensemble pseudo-energy EE. Finally, at process block 865, the ensemble pseudo-energy EE has been determined and can be stored or returned, following which the method terminates.

Many variations are possible. In examples, any loop or the global energy calculation could be omitted.

XI. Example Data Vectors

Figure 9:
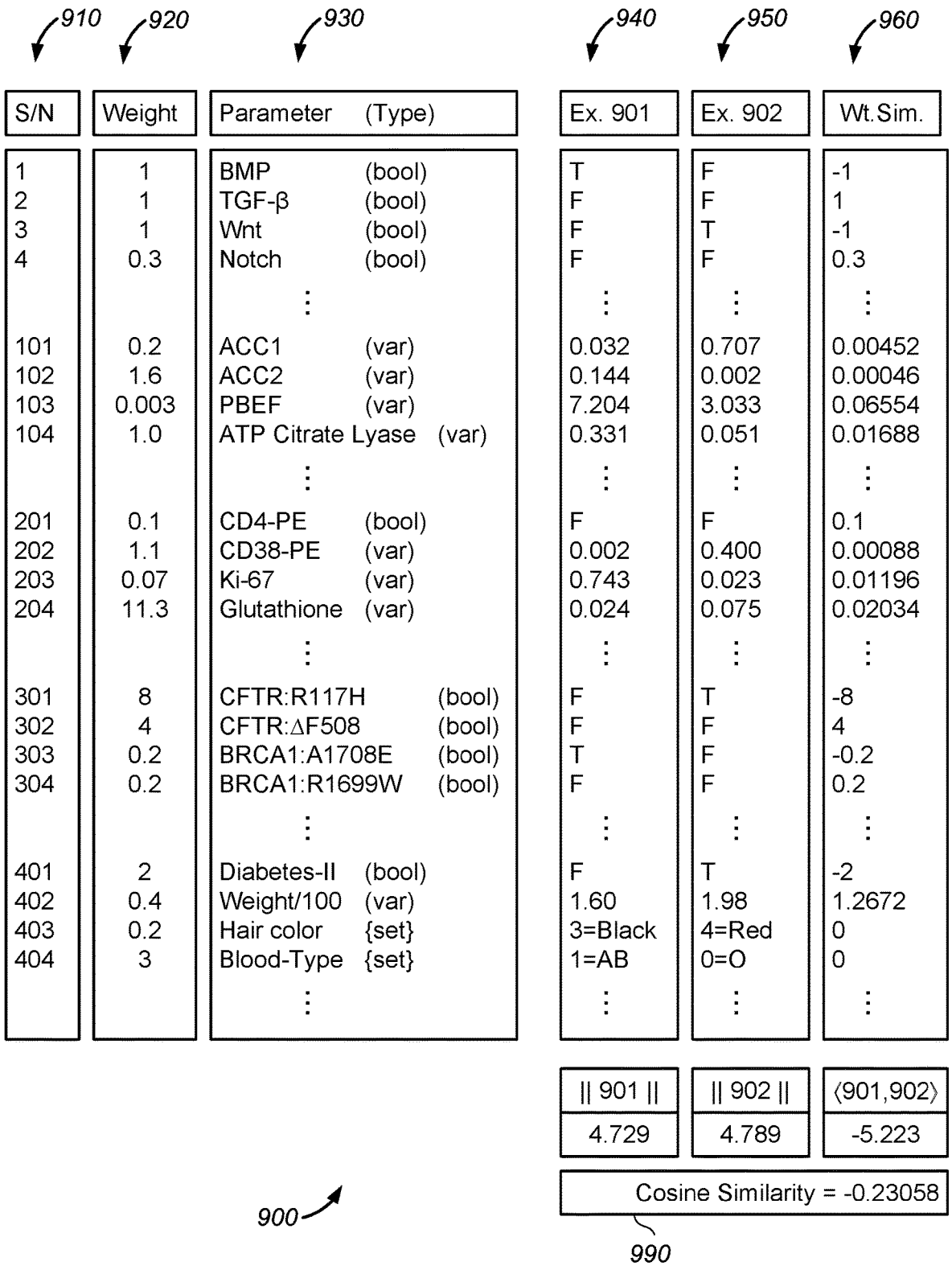
FIG. 9 is a diagram depicting example biological sample data vectors, according to disclosed technology.

FIG. 9 is a diagram 900 depicting example biological sample data vectors, according to disclosed technology. In diagram 900, the description of example data vector components is presented. Two example data vectors are shown, and an exemplary calculation of a cosine similarity measure is illustrated.

Column 930 provides a description of 20 exemplary vector components, grouped by fours according to the type of attribute represented by each component. Column 910 provides default serial numbers of these coefficients for convenience of discussion. Components 1-4 are example indicators of gene expression: BMP (bone morphogenetic protein); TGF-β (transforming growth factor); Wnt (a protein of the Wnt signaling pathway); and Notch (a receptor of the Notch signaling pathway). Which gene expression or other features will be selected depends on the specifics of the system under study; no a priori assumptions are needed. In this illustration, all are represented as Boolean variables, wherein True, On, or 1 can be used to represent that a particular gene expression is above a preselected threshold (such as a baseline gene expression level from control subjects'), while False, Off, or 0 can be used to represent that the gene expression is below a preselected threshold (such as a control gene expression level from healthy subjects or cells in a baseline experimental condition). For computational convenience, the actual values used to represent the variables can be scaled or offset. For example, if a gene is expressed 10% of the time in a population, On can be represented by the value 0.9 and Off can be represented by −0.1 to provide a zero mean.

Components 101-104 are indicators of metabolic enzymes: ACC1 and ACC2 (acetyl-coenzymes A), PBEF (Nicotinamide Phosphoribosyltransferase), and ATP Citrate Lyase (ATP being adenosine triphosphate). In this illustration, all are represented as continuous variables, indicative of their concentration or activity level.

Components 201-204 are cytometric measurements: CD4-PE (a monoclonal antibody); CD38-PE (another monoclonal antibody); ki-67 (a cellular marker for proliferation); and glutathione (a tripeptide antioxidant). CD4-PE is observed bimodally and is represented as a Boolean variable in this illustration, while the other three components are represented as continuous variables.

Components 301-304 are mutations: CFTR:R117H and CFTR:ΔF508 are mutations of the CFTR (Cystic fibrosis transmembrane conductance regulator) gene and are associated with cystic fibrosis; BRCA1:A1708E and BRCA1:R1699W are mutations of the BRCA1 (breast cancer 1) gene and are associated with breast cancer. Presence or absence of these mutations are encoded as Boolean values in this illustration. In other examples, mutations of e.g. an "A" base can be represented as a coded set, for example no mutation can be encoded as 0, mutations to C, G, T can be encoded as 1, 2, and 3 respectively, and encodings 4 and 5 can be used for an insertion or a deletion respectively.

Finally, components 401-404 represent non-cellular observables or attributes of the biological sample: Diabetes-II can indicate the disease state (presence or absence) of diabetes type II as a Boolean variable; weight in units of 100 lbs indicates an individual's weight, for example an individual weighing 160 lbs can have weight/100=1.60; hair color indicates an individual's natural hair color, and is represented as a coded set, for example 0=black, 1=brown, 2=blonde, 3=red; and blood-type indicates an individual's standard blood type, which can also be represented as a coded set, e.g. 0=type 0, 1=type A, 2=type B, 3=type AB.

Column 920 provides example normalization coefficients for the illustrated vector components, which can be selected to vary according to the type of variable used to represent the component, and can vary further according to the importance or amplitude levels of each specific component.

Columns 940 and 950 provide two example data vectors 901 and 902 according to the schema of column 930. Each component of data vectors 901 and 902 have values appropriate for the type of the component. Column 960 illustrates the component-wise inner product calculation for $\langle 901, 902 \rangle$. In this illustration, the inner product term for continuous variables and Boolean variables is simply given by $g_k \cdot 901_k \cdot 902_k$ for the $k^{th}$ component, where 0 and 1 are used to represent Off (or, Absent) and On (or, Present) states of Boolean variables. Inner products for coded sets can be calculated as 1 if the coded values are the same and 0 if the coded values are different, multiplied by the corresponding normalization coefficient g. In other examples, other inner product definitions can be used, such as 0.5 g for the similarity between blood types A and AB.

At the bottom of column 960, the inner product $\langle 901, 902 \rangle$ is calculated by summing the component-wise contributions in the column above. Assuming that the 20 components shown are the only components of the data vectors illustrated, the inner product is found to be −5.223. The norm $\|901\|$ is calculated by summing $g_k \cdot 901_k \cdot 901_k$ over the components and taking the square root, to obtain $\|901\|=4.729$. Similarly, the norm $\|902\|=4.789$ can be determined.

Finally, box 990 shows the cosine similarity between vectors 901 and 902, $$S = \frac{\langle 901 \cdot 902 \rangle}{\|901\| \cdot \|902\|} = \frac{-5.2233}{4.729 \cdot 4.789} = -0.2306$$

XII. Example Partitions and Example Operations

Figure 10:
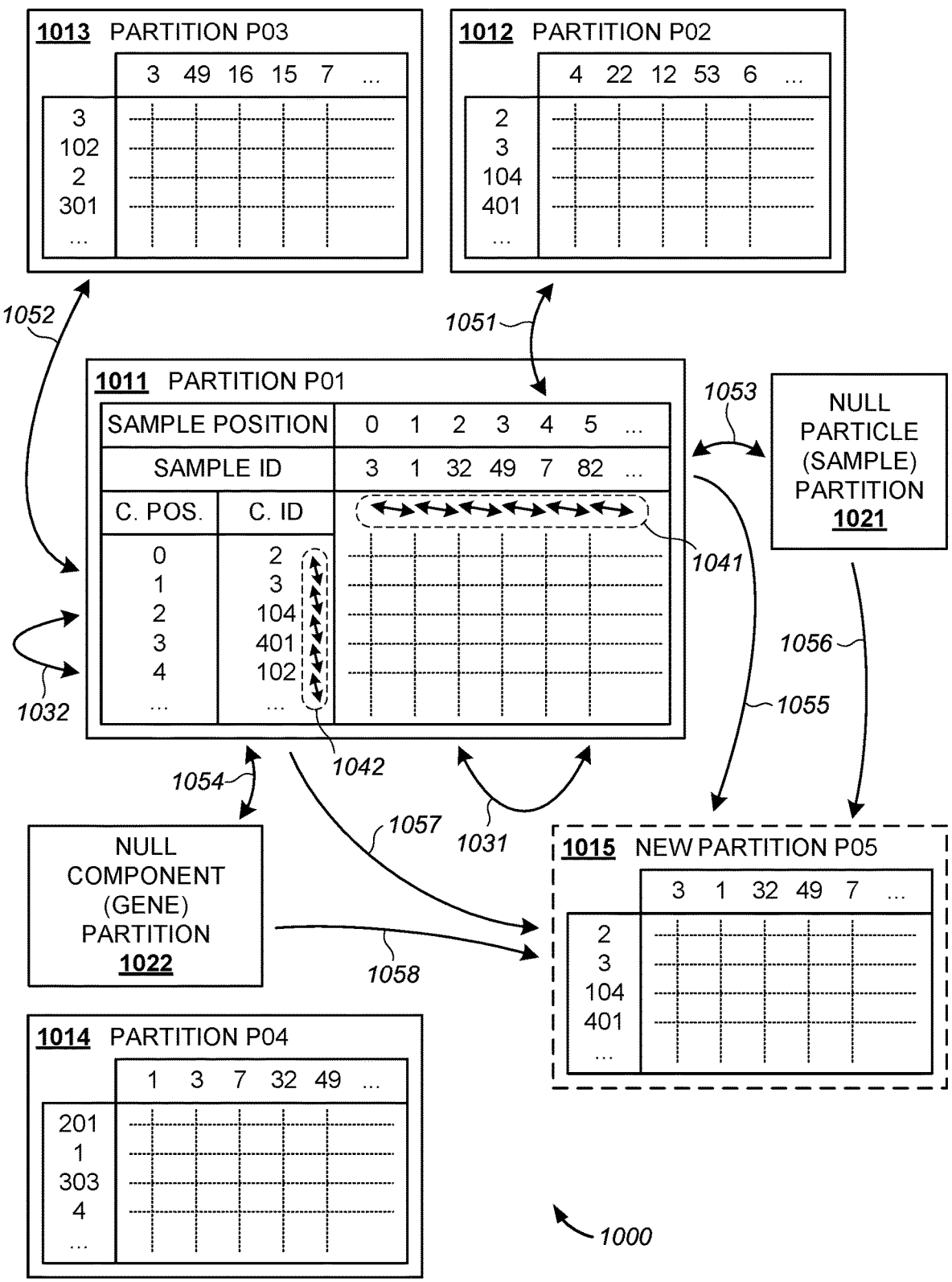
FIG. 10 is a diagram depicting example partitions and optimization procedure operations, according to disclosed technology. Active partitions having different relationships are depicted, along with null partitions and a new partition. With reference to these partitions, three types of operations are depicted: random intra-partition Monte Carlo operations, random inter-partition Grand Canonical operations, and deterministic intra-partition dynamic evolution operations.

FIG. 10 is a diagram 1000 depicting example partitions 1011-1015, 1021-1022 and operations 1031-1032, 1041-1042, 1051-1058 according to disclosed technology. Active partitions 1011-1014 having different relationships are depicted, along with null partitions 1021-1022 and a new partition 1015. With reference to these partitions, three types of operations are depicted: random intra-partition Monte Carlo operations 1031-1032, random inter-partition Grand Canonical operations 1051-1056, and deterministic intra-partition dynamic evolution operations 1041-1042.

Active partition 1011 is organized as a two-dimensional array having rows and columns shown by dotted lines. Each dotted line column represents the data vector of a particle in the partition, which in turn can represent a biological sample. The particles are labeled, according to their corresponding biological sample, in the row marked "Sample ID" and have corresponding pseudo-positions indicated in the row marked "Sample position." As shown, the particle at position 0 represents biological sample number 3, and the particles at positions 1-5 represent samples 1, 32, 49, 7, and 82 respectively. Each dotted line row represents a component of the data vector. The components are labeled according to their serial number as shown in the column labeled "C. SN." For purposes of illustration, these serial numbers match the serial numbers of column 910 in FIG. 9. Due to rearrangement of components, the components can occupy index positions that differ from their native serial number; these indices are shown in the column labeled "C. INDX." As shown, index 0 contains the values for data vector component 2, which can be a gene expression, e.g., TGF-$\beta$. Similarly, component indices contain values for components 3 (gene expression Wnt), 104 (enzyme ATP Citrate Lyase), 401 (disease state Diabetes-II), and 102 (enzyme ACC2) respectively. Active partition 1011 can have many more rows and columns than illustrated: hundreds, thousands, or millions, of columns for corresponding samples; and thousands, millions, or even billions of rows for data vector components.

Active partitions 1012-1014 are illustrated similarly, with four rows shown for component indices 0-3 and five columns for one-dimensional pseudo-positions 0-4. For compactness of illustrations some labeling, component index, and sample position fields are omitted for partitions 1012-1015; these omitted parts can be understood to follow partition 1011.

As illustrated, active partition 1012 has the same components as active partition 1011 at component indices 0-3, and a disjoint set of particles compared with active partition 1011. The relationship between active partitions 1011-1012 illustrates an example where data vector components are commonly ordered in both partitions, and a biological sample is represented in only one of the partitions.

Active partition 1013 has a partial overlap of biological samples with active partition 1011: biological samples 3, 49, and 7 occur at pseudo-positions 0, 1, and 4 of active partition 1013, and also occur at pseudo-positions 0, 3, and 4 of active partition 1011. The remaining biological samples 1, 32, 82, 16, and 15 are not replicated between these two partitions. Active partition 1013 also has a partial overlap of data vector components with active partition 1011: components 2, 3, and 102 occur at index 0, 1, and 4 of active partition 1011, and also occur at index 2, 0, and 1 of active partition 1013.

Active partitions 1014 and 1011 have particles representing common biological samples 3, 1, 32, 49, and 7, albeit arranged in a different order. Active partitions 1014 and 1011 have disjoint sets of vector components. Thus through the operations described, different feature sets can be obtained with the same particles, from different subspaces of the high-dimensional data vectors.

Finally a new active partition 1015 is shown, with no particles and no data vector components assigned.

A conventional grand canonical ensemble is open to particles entering or leaving the ensemble. As a computational artifact, this can be incorporated into a disclosed grand canonical ensemble model by introducing a null partition for non-interacting particles. A null partition 1021 can contain non-interacting particles and could have no pseudo-energy measure defined; the null partition allows data vectors of biological samples to be preserved within the computational environment even when the corresponding particles have escaped from any interactions. Because particles in a null partition 1021 are non-interacting, position and organization of particles in a null partition are not meaningful and are not illustrated in FIG. 10, although in a computational environment the particles in a null partition can nevertheless be stored in some order.

In some examples, data vector components can be moved among partitions similarly to particles; a null partition 1022 for data vector components can be provisioned similarly. Null partition 1022 allows attributes of particular genes or gene expressions to be discounted or removed from one, multiple, or all active partitions. In other examples, all data vector components are retained in every partition (although some components can be pushed down to very high component indices where a similarity weighting function has insignificant weight), and no null component partition 1022 is required.

Turning to randomized operations, arrow 1031 illustrates a basic intra-partition particle swap, which can be a Monte Carlo operation and can be accepted or rejected according to a thermodynamic criterion such as a Metropolis criterion. In some examples, randomized component index swaps can also be supported, as indicated by arrow 1032. Like the particle swap 1031, the component index swap 1032 can also be a Monte Carlo operation and can be accepted or rejected according to a thermodynamic criterion.

In examples, deterministic operations can also be supported within an active partition as described herein. The arrow set 1041 depicts conditional pseudo-position swaps among neighboring particle pairs. The arrow set 1042 depicts conditional index swaps among neighboring vector components.

Another class of operations is dubbed GC operations; these are randomized operations that move items in or out of, or between, partitions. Arrow 1051 shows a basic move of a particle out of active partition 1011 and into active partition 1012, or vice versa. The GC operation of arrow 1051 can be a single particle movement; the arrow is drawn bidirectionally for convenience of illustration to indicate that the operation can be performed in either direction. In examples, addition of a particle into an active partition can be at a selected location. By way of illustration, the particle for sample 7 in active partition 1011 can be moved out of active partition 1011 (causing the particle of sample 82 to be shifted leftward to close the ensuing gap); this particle can be introduced into active partition 1012 between samples 12 and 53 (causing the particles of samples 53 and 6 to be shifted to the right). Arrow 1052 shows a similar move of a component that can be deleted from one active partition and added at a selected index into another active partition. As with particle moves, bidirectional arrow 1052 indicates that a move can be performed in either direction.

In an analogous manner, arrows 1053 and 1054 show a movement of a particle or a vector component to or from corresponding null partitions 1021 and 1022 respectively.

In examples, operations can include creation of a new active partition 1015. Arrows 1055 and 1056 show movement of a particle into a newly created partition 1015, from an active partition 1011 or a null partition 1021 respectively. In some examples, movement of vector components between partitions is supported, and arrows 1057 and 1058 show movement of a vector component into a newly created partition, from an active partition 1011 or a null partition 1022 respectively.

In some examples, only the components already instantiated in the destination partition are implemented for the moved particle, while in other examples all data vector components of the particle can be instantiated when a particle is moved into another partition. In further examples, other protocols can be employed, such as moving a particle with no components into a new partition 1015, and requiring components to be instantiated in the new partition 1015 by a component movement operation. Similar to particle movements, different protocols can be used for carrying particles when components are moved.

In some examples, redundant particles are allowed, and the same biological sample can be represented by different particles in respective active partitions. In such examples, the available operations can also include a copy operation (without removal of the original particle from the source partition) or a delete operation (without insertion of the deleted particle into the destination partition). In examples, deletion of a sole remaining particle of a given biological sample can result in the deleted particle automatically being added to the null partition 1022.

The description of diagram 1000 above encompasses numerous variants. With this disclosure in hand, one of ordinary skill will appreciate that many additional variations are possible within the scope of disclosed technologies, as described herein.

XIII. Example Methods for Facilitating Cell-Based Therapies

Figure 11:
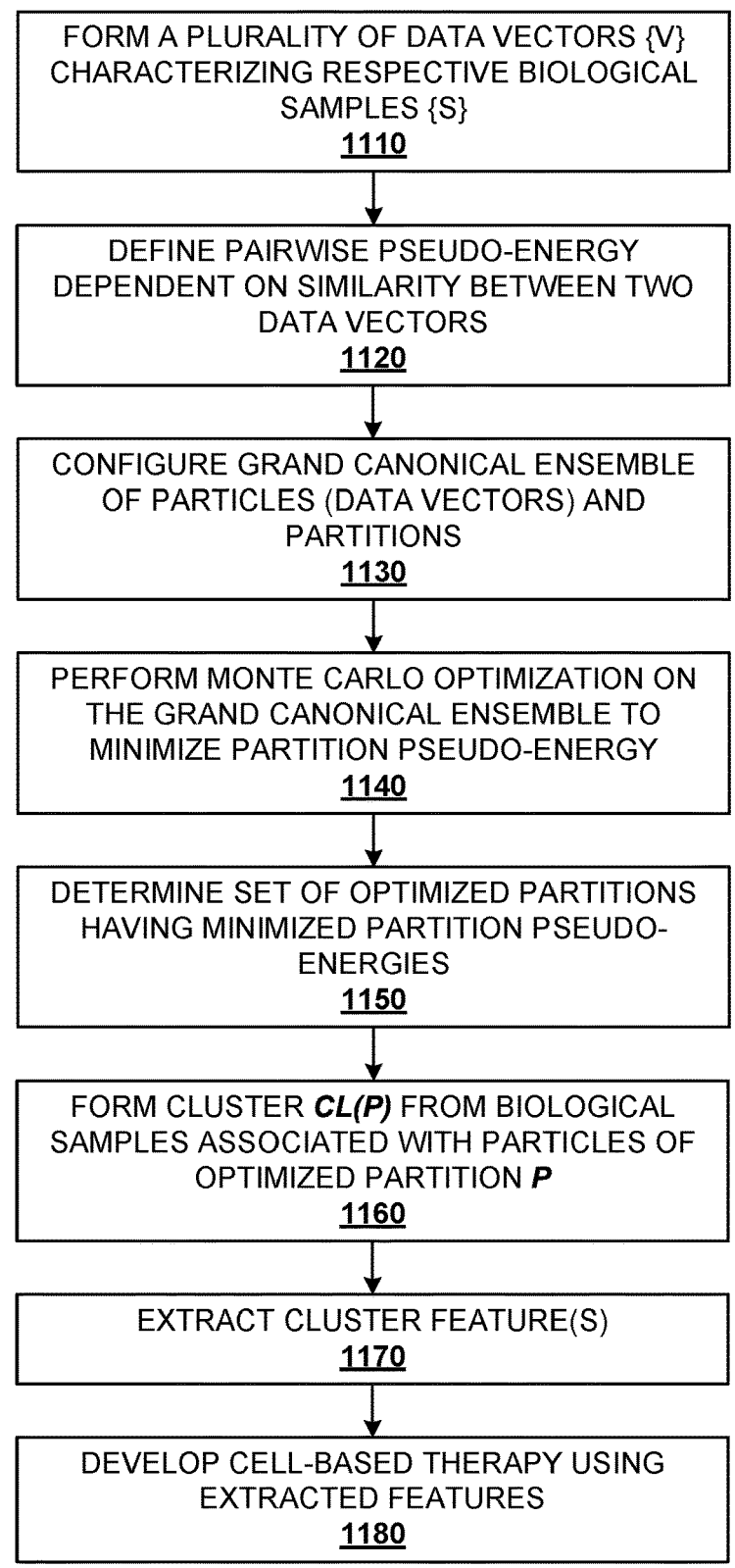
FIG. 11 is a flowchart depicting an example method for characterizing cell-based therapies, according to disclosed technology.

FIG. 11 is a flowchart 1100 depicting an example method for developing cell-based therapies, according to disclosed technology. At process block 1110, a plurality of data vectors can be formed. Each data vector can have at least $10^6$ components, some of which can be Boolean variables representing NGS read data (such as gene expression or another bimodal transcriptome parameter), and at least one of which can be an indication of a disease state. Similarly, hundreds, thousands, or millions of such vectors can be analyzed. In other examples, data vectors of less than $10^6$ components can be used.

In optional process block 1120, a pairwise pseudo-energy can be defined. The pairwise pseudo-energy depends on and is a measure of similarity between two data vectors, and in examples can be an inverse similarity such as minus one times a weighted cosine similarity between the two vectors.

At process block 1130, a grand canonical ensemble model can be configured, comprising one or more partitions, which can represent phases of the ensemble, and a plurality of particles, each particle representing and described by a respective data vector. Through its data vector, each particle is associated with a respective biological sample. In some examples, particles can be constrained to be unique, and each biological sample can have at most one particle in the ensemble. In other examples, a biological sample can be associated with multiple particles, reflecting the fact that a biological sample can be a part of multiple clusters with respect to different features and subspaces of the high-dimensional space of the vector components. In some examples, particles can be copied or deleted.

At process block 1140, a Monte Carlo procedure can be performed on the grand canonical ensemble. In some examples, the procedure can be directed to concurrent reduction or minimization of pseudo-energies of one or more partitions, or even all non-empty active partitions. The partition pseudo-energy can be a sum over pairwise pseudo-energies of all pairs of particles in the partition, and/or is a measure of similarity between the particles of the partition. In other examples, the optimization can be directed to minimization of a total pseudo-energy of the grand canonical ensemble over all active partitions.

In some examples, the optimization can include only randomized Monte Carlo operations, while in other examples Monte Carlo operations can be combined or mixed with deterministic operations. In examples, the particles are variably disposed among partitions, and can be moved among partitions through optimization operations. In examples, partitions can be created or deleted during the optimization procedure. In examples, the optimization method can include simulated annealing.

At process block 1150, the Monte Carlo procedure leads to determination of a set of optimized partitions. In some examples, each optimized partition can have individually minimized pseudo-energy, while in other examples the optimized partitions are such that the total ensemble pseudo-energy is minimized.

At process block 1160, each optimized partition P is used to form a respective cluster CL(P) incorporating representations of the biological samples associated with the particles of the optimized partition P. In some examples, one or more clusters are formed from respective optimized partitions, rather than from all optimized partitions.

At process block 1170, features are extracted from one or more cluster. Feature extraction can be performed, for example, by a technique based on linear discriminant analysis. The features of a cluster can include, for example, a disease state along with a gene expression, or the ability to produce a beneficial (or harmful) in vivo effect in a pre-clinical disease model or a human subject. Finally, at process block 1180, the extracted features are used to facilitate the development of at least one cell-based therapy. To illustrate this point further, a cell therapy product could require the presence of more than one distinct cell type in defined proportions to be effective. Conversely, it could require absence of potentially harmful cells, such as undifferentiated stem cells with the capacity to form tumors, to be safe. Thus, methods to evaluate cell therapy products by enumerating the specific subpopulations they contain, defined herein by the partitions identified by the disclosed technology, are likely to play a significant role in the successful development of these products.

Many variations are possible. For example, the data vector can include some components which representing gene mutation data, and at least component which indicates a disease state. The data vector can have any number of components limited only by the available memory in a computing system where the application is running.

XIV. Applications

While exemplary applications of the disclosed technology can be described in the context of NGS and other data of single cells and other biological samples, the disclosed technology is not so limited. The biological application can be readily extended to medical records, another domain in which very high dimensional data is in need of efficient classification and clustering technology.

Other domains featuring very high dimensional data include data networks (including the conventional Internet and a potentially larger Internet-of-Things) where clustering has applicability to security and threat assessment and remediation. The domain of Internet content is another high-dimensional domain, where clustering is applicable in the areas of rights management (e.g. for detecting copies), search (text, images, audio, or semantic). High dimensional clustering can also be applicable to communication networks, e.g. for identifying clusters of mobile phones or social media users for security and social media applications, and for organizing ad hoc networks.

The disclosed technology has other advantages besides handling high-dimensional problems, which can lead to further applications. For example, the disclosed technology is suitable for handling bimodal and statistically ill-conditioned data. As such, applications can be found in the domains of economics, finance, image processing, linguistics, political science, and many others.

XV. Additional Features

Feature extraction can alternatively be performed by a naïve comparison technique, a support vector machine, a state vector machine, linear discriminant analysis (LDA), principal component analysis (PCA), nonlinear principal component analysis, or independent component analysis (ICA).

An improvement procedure directed to minimization of one or more pseudo-energy measures can include any combination of an optimization procedure, simulated annealing, a Monte Carlo procedure, deterministic evolution, particle movements between partitions, or other processes analogous to grand canonical ensemble phase transitions.

Data vectors described herein can incorporate or be derived from one or more of: a component representing gene expression of a cell of the respective biological sample; a component representing a quantity of a protein within a cell of the respective biological sample; a component representing a mutation of a gene of a cell of the respective biological sample; a component representing a binary or bimodal attribute of a single cell of the respective biological sample; a component representing a binary or bimodal attribute of the respective biological sample; a component represented as a Boolean variable; a component represented as a continuous variable; or a component represented as a discrete coded variable.

The number of components in a data vector can exceed a number of the biological samples.

Pseudo-energy measures can include one or more of: a cosine similarity function; a component-wise Boolean similarity score; a Euclidean pseudo-distance; a Manhattan pseudo-distance; a Jaccard similarity function; a correlation score; an inversion operator; a weighting function dependent on component; a weighting function dependent on component index; or a weighting function dependent on pseudo-distance between two data vectors in a partition.

The weighting function can be dependent on pseudo-distance between two data vectors in a partition, according to one or more of: the weighting function is inversely proportional to a square of the pseudo-distance; the weighting function is inversely proportional to the pseudo-distance; the weighting function has the form of a Lennard-Jones potential, a 6-9 Lennard-Jones potential, a modified Lennard-Jones potential, or a Morse potential; the weighting function is segmented; the weighting function is piecewise continuous; or the weighting function takes positive and negative values.

A Monte Carlo procedure or iterative improvement procedure can include one or more of the following operations: a random or Monte Carlo swap of two particles within a partition; a deterministic change in positions of two or more particles within a partition; a random or Monte Carlo swap of two component positions within a partition; a deterministic change in positions of two or more components within a partition; a jump of a particle from a first partition to a second partition; a jump of a component from a first partition to a second partition; a duplication of a particle at a first position within a first partition into a chosen second position within a second partition; a split of a particle into a first particle portion within a first partition and a second particle portion within a second partition; a creation of a new partition; a deletion of an empty partition; a consolidation of two or more partitions into a single partition; a split of an existing partition into two or more partitions; a selective acceptance of an operation based at least in part on a pseudo-temperature; a selective acceptance of an operation according to a Metropolis criterion; a change in the pseudo-temperature according to a predetermined criterion, a predetermined pattern, or a schedule; an operation that is statistically uncorrelated with a preceding operation; an operation that is scheduled deterministically; or an operation that is scheduled based on criteria reflecting a state of the grand canonical ensemble.

Particle positions within a partition can be organized in a vector space having a dimensionality in a range 1, 2, 3, 4-10, 11-100, 101-1000, or 1,001-10,000. The particles can be organized in a Cartesian space. Pseudo-distances between particles can be determined according to Euclidean, Manhattan, or Chebyshev distance. The particles can be organized in a non-Cartesian space. Pseudo-distances between particles can be determined according to a non-Cartesian distance metric.

Each active partition can be associated with a same pseudo-energy measure. Each active partition can be associated with a same form of pseudo-energy measure. At least two active partitions can be respectively associated with two distinct pseudo-energy measures. At least two active partitions can be associated respectively with two distinct forms of pseudo-energy measures. A Monte Carlo procedure or iterative improvement procedure can be directed to independent minimization of respective pseudo-energy measures of each active partition. A grand canonical ensemble can be associated with one global pseudo-energy measure. The global pseudo-energy measure can include an energy cost for all active partitions irrespective of energy states within each separate active partition. The global pseudo-energy measure can incorporate an energy cost, for at least a first active partition, that is independent of similarities between data vectors of particles in the first active partition. The global pseudo-energy measure can include one or more energy cost terms selected to steer the Monte Carlo procedure or iterative improvement procedure away from undesirable extrema. The Monte Carlo procedure or iterative improvement procedure can be directed to minimization of the global pseudo-energy measure.

The Monte Carlo procedure or iterative improvement procedure is performed in one or more of the following modes. Each data vector can be identified with exactly one particle in the grand canonical ensemble. A data vector can be present concurrently in two or more partitions. A first component of a first data vector can be present in at most one partition in the grand canonical ensemble. After determining one or more of the selected partitions, the grand canonical ensemble can continue to evolve without reset. After determining one or more of the selected partitions, the grand canonical ensemble can be restarted with a randomized reset. After determining one or more of the selected partitions, the grand canonical ensemble can be restarted with a predetermined reset state.

XVI. Example Computing Environment

Figure 12:
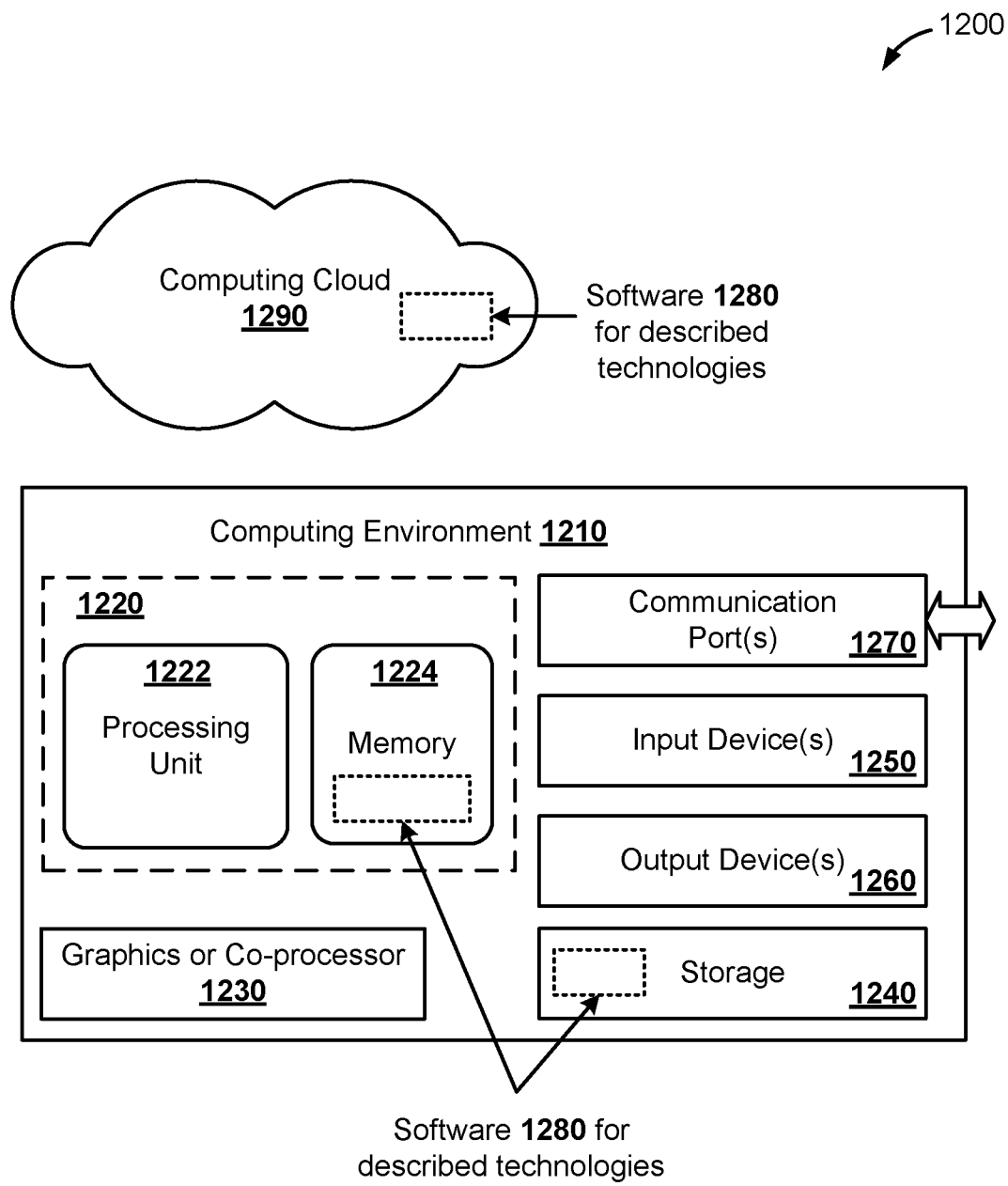
FIG. 12 illustrates a generalized example of a suitable computing environment in which described embodiments, techniques, and technologies, including performing classification, can be implemented.

FIG. 12 illustrates a generalized example of a suitable computing system 1200 in which described examples, techniques, and technologies, including clustering of biological samples, or improvement or optimization of a grand canonical ensemble, can be implemented. For example, the computing system 1200 can implement all of the functions described with respect to FIGS. 1-11, as described herein.

The computing system 1200 is not intended to suggest any limitation as to scope of use or functionality of the technology, as the technology can be implemented in diverse general-purpose or special-purpose computing environments. For example, the disclosed technology can be implemented with other computer system configurations, including hand held devices, multiprocessor systems, microprocessor-based or programmable consumer electronics, network PCs, minicomputers, mainframe computers, parallel computing systems, and the like. The disclosed technology can also be practiced in distributed computing environments where tasks are performed by remote processing devices that are linked through a communications network. In a distributed computing environment, program modules can be located in both local and remote memory storage devices.

With reference to FIG. 12, the computing environment 1210 includes at least one central processing unit 1222 and memory 1224. In FIG. 12, this most basic configuration 1220 is included within a dashed line. The central processing unit 1222 executes computer-executable instructions and can be a real or a virtual processor. In a multi-processing system, multiple processing units execute computer-executable instructions to increase processing power and as such, multiple processors can be running simultaneously. The memory 1224 can be volatile memory (e.g., registers, cache, RAM), non-volatile memory (e.g., ROM, EEPROM, flash memory, etc.), or some combination of the two. The memory 1224 stores software 1280 that can, for example, implement the technologies described herein. Computing environment 1210 can also include a graphics processing unit or co-processing unit 1230.

A computing environment can have additional features. For example, the computing environment 1200 includes storage 1240, one or more input devices 1250, one or more output devices 1260, and one or more communication connections 1270. An interconnection mechanism (not shown) such as a bus, a controller, or a network, interconnects the components of the computing environment 1200. Typically, operating system software (not shown) provides an operating environment for other software executing in the computing environment 1200, and coordinates activities of the components of the computing environment 1200.

The storage 1240 can be removable or non-removable, and includes magnetic disks, magnetic tapes or cassettes, CD-ROMs, CD-RWs, DVDs, or any other medium which can be used to store information and that can be accessed within the computing environment 1200. The storage 1240 stores instructions for the software 1280 and measurement data, which can implement technologies described herein.

The input device(s) 1250 can be a touch input device, such as a keyboard, keypad, mouse, touch screen display, pen, or trackball, a voice input device, a scanning device, or another device, that provides input to the computing environment 1210. The input device(s) 1250 can also include interface hardware for connecting the computing environment to control and receive data from host and client computers, storage systems, measurement acquisition components, sequencers, other NGS data sources, control excitation sources, or to display or output data processed according to methods disclosed herein, including data acquisition systems coupled to a plurality of sensors.

For audio, the input device(s) 1250 can be a sound card or similar device that accepts audio input in analog or digital form, or a CD-ROM reader that provides audio samples to the computing environment 1200. The output device(s) 1260 can be a display, printer, speaker, CD-writer, or another device that provides output from the computing environment 1210.

The communication connection(s) 1270 enable communication over a communication medium (e.g., a connecting network) to another computing entity. The communication medium conveys information such as computer-executable instructions, compressed graphics information, video, or other data in a modulated data signal.

Some examples of the disclosed methods can be performed using computer-executable instructions implementing all or a portion of the disclosed technology in a computing cloud 1290. For example, construction of data vectors and configuration of a grand canonical ensemble can be executed locally in the computing environment (e.g., by a measurement acquisition component), while optimization of the grand canonical ensemble can be performed on remote servers located in the computing cloud 1290.

Computer-readable media are any available media that can be accessed within a computing environment 1200. By way of example, and not limitation, with the computing environment 1210, computer-readable media include memory 1220 and/or storage 1240. As should be readily understood, the term computer-readable storage media includes the media for data storage such as memory 1220 and storage 1240, and not transmission media such as modulated data signals.

The present innovations can be described in the general context of computer-executable instructions, such as those included in program modules, being executed in a computing system on a target real or virtual processor. Generally, program modules or components include routines, programs, libraries, software objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

The terms "system," "environment," and "device" are used interchangeably herein. Unless the context clearly indicates otherwise, none of these terms implies any limitation on a type of computing system, computing environment, or computing device. In general, a computing system, computing environment, or computing device can be local or distributed, and can include any combination of special-purpose hardware and/or general-purpose hardware and/or virtualized hardware, together with software implementing the functionality described herein. Virtual processors, virtual hardware, and virtualized devices are ultimately embodied in one or another form of physical computer hardware.

XVII. Example Cloud Computing Environment

Figure 13:
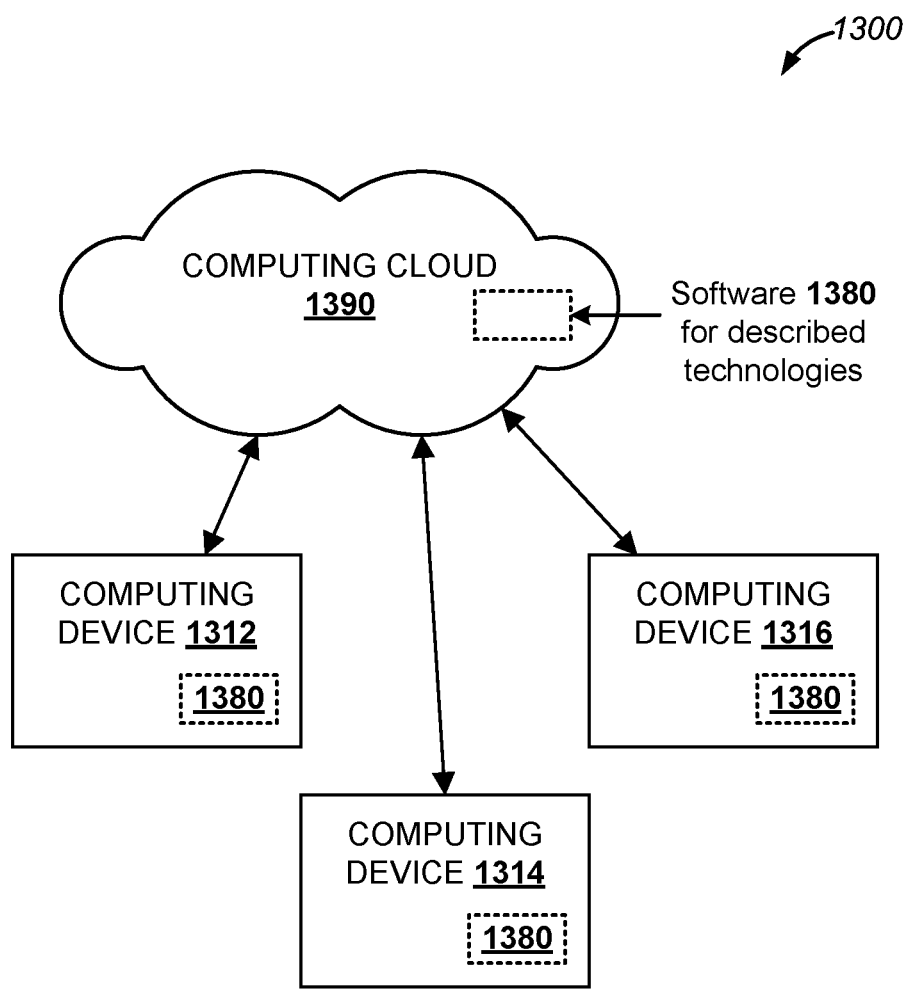
FIG. 13 is a diagram schematically depicting computing devices operating in conjunction with a computing cloud for implementation of disclosed technologies.

FIG. 13 depicts an example cloud computing environment 1300 in which the described technologies can be implemented. The cloud computing environment 1300 comprises a computing cloud 1390 containing resources and providing services. The computing cloud 1390 can comprise various types of cloud computing resources, such as computer servers, data storage repositories, networking resources, and so forth. The computing cloud 1390 can be centrally located (e.g., provided by a data center of a business or organization) or distributed (e.g., provided by various computing resources located at different locations, such as different data centers and/or located in different cities or countries).

The computing cloud 1390 can be operatively connected to various types of computing devices (e.g., client computing devices), such as computing devices 1312, 1314, and 1316, and can provide a range of computing services thereto. One or more of computing devices 1312, 1314, and 1316 can be computers (e.g., server, virtual machine, embedded systems, desktop, or laptop computers), mobile devices (e.g., tablet computers, smartphones, or wearable appliances), or other types of computing devices. Connections between computing cloud 1390 and computing devices 1312, 1314, and 1316 can be over wired, wireless, or optical links, or any combination thereof, and can be short-lived or long-lasting. These connections can be stationary or can move over time, being implemented over varying paths and having varying attachment points at each end. Computing devices 1312, 1314, and 1316 can also be connected to each other.

Computing devices 1312, 1314, and 1316 can utilize the computing cloud 1390 to obtain computing services and perform computing operations (e.g., data processing, data storage, and the like). Particularly, software 1380 for performing the described innovative technologies can be resident or executed in the computing cloud 1390, in computing devices 1312, 1314, and 1316 (and any number of additional devices to allow for parallel processing of the computing operations described herein), or in a distributed combination of cloud and computing devices.

XVIII. General Considerations

As used in this application the singular forms "a," "an," and "the" include the plural forms unless the context clearly dictates otherwise. Additionally, the term "includes" means "comprises." Further, the term "coupled" encompasses mechanical, electrical, magnetic, optical, as well as other practical ways of coupling or linking items together, and does not exclude the presence of intermediate elements between the coupled items. Furthermore, as used herein, the term "and/or" means any one item or combination of items in the phrase.

The systems, methods, and apparatus described herein should not be construed as being limiting in any way. Instead, this disclosure is directed toward all novel and non-obvious features and aspects of the various disclosed embodiments, alone and in various combinations and subcombinations with one another. The disclosed systems, methods, and apparatus are not limited to any specific aspect or feature or combinations thereof, nor do the disclosed things and methods require that any one or more specific advantages be present or problems be solved. Furthermore, any features or aspects of the disclosed embodiments can be used in various combinations and subcombinations with one another.

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed things and methods can be used in conjunction with other things and methods. Additionally, the description sometimes uses terms like "accept," "accumulate," "analyze," "apply," "assign," "attain," "calculate," "change," "complete," "configure," "control," "copy," "defines," "delete," "determine," "display," "estimate," "execute," "extract," "follow," "generate," "improve," "instantiate," "iterate," "log," "minimize," "modify," "move," "optimize," "proceed," "produce," "randomize," "record," "reject," "restart," "return," "select," "store," "swap," "take effect," or "vary" to describe the disclosed methods. These terms are high-level abstractions of the actual operations that are performed. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the disclosed methods can be implemented using computer-executable instructions stored on one or more computer-readable media (e.g., non-transitory computer-readable media, such as one or more optical media discs, volatile memory components (such as DRAM or SRAM), or nonvolatile memory components (such as flash drives or hard drives)) and executed on a computer (e.g., any commercially available computer, including smart phones or other mobile devices of adequate capacity that include computing hardware). Any of the computer-executable instructions for implementing the disclosed techniques, as well as any data created and used during implementation of the disclosed embodiments, can be stored on one or more computer-readable media (e.g., non-transitory computer-readable media). The computer-executable instructions can be part of, for example, a dedicated software application, or a software application that is accessed or downloaded via a web browser or other software application (such as a remote computing application). Such software can be executed, for example, on a single local computer (e.g., as a process executing on any suitable commercially available, proprietary, hosted, or dedicated computer system, including a computing cluster or a supercomputer) or in a network environment (e.g., via the Internet, a wide-area network, a local-area network, a client-server network (such as a cloud computing network), or other such network) using one or more networked computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C, C++, Common Lisp, Dylan, Erlang, Fortran, Go, Haskell, Java, JavaScript, *Julia*, Python, Scheme, or any other suitable programming language. Likewise, the disclosed technology is not limited to any particular computer or type of hardware. Certain details of suitable computers and hardware are well-known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Having described and illustrated the principles of our innovations in the detailed description and accompanying drawings, it will be recognized that the various examples can be modified in arrangement and detail without departing from such principles.

In view of the many possible examples to which the principles of the disclosed technology can be applied, it should be recognized that the illustrated examples are only preferred examples and should not be taken as limiting the scope of the disclosed technology. Rather, the scope of the claimed subject matter is defined by the following claims.

We claim:

1. A computer-implemented method for classifying biological samples, comprising:
   constructing a plurality of data vectors characterizing respective biological samples and comprising components representing attributes of the respective biological samples;
   defining one or more measures representative of similarity between data vectors of the plurality of data vectors;
   by one or more computer processors having memory attached thereto:
      performing an iterative improvement procedure on a grand canonical ensemble comprising a plurality of particles variably distributed among two or more partitions, the particles representing respective data vectors of the plurality of data vectors, and the iterative improvement procedure enhancing the one or more measures; and
      determining, from the iterative improvement procedure, a set of selected partitions of the particles having increased similarity between the data vectors of the particles in each selected partition, to classify the biological samples.

2. The computer-implemented method of claim 1, wherein each particle is associated with a respective one of the biological samples.

3. The computer-implemented method of claim 1, wherein the performing an iterative improvement procedure comprises performing a Monte Carlo procedure on the multi-partition grand canonical ensemble to reduce pseudo-energy of a plurality of the partitions by redistributing the particles and/or the components of the data vectors among the plurality of partitions, wherein the pseudo-energy of a given partition is a measure of similarity between the particles of the given partition, and wherein reduced pseudo-energy corresponds to the increased similarity.

4. The computer-implemented method of claim 3 wherein the Monte Carlo procedure or iterative improvement procedure includes two or more of the following operations:
   a random or Monte Carlo swap of two particles within a partition;
   a deterministic change in positions of two or more particles within a partition;
   a random or Monte Carlo swap of two component positions within a partition;
   a deterministic change in positions of two or more components within a partition;
   a jump of a particle from a first partition to a second partition;
   a jump of a component from a first partition to a second partition;
   a duplication of a particle at a first position within a first partition into a chosen second position within a second partition;
   a split of a particle into a first particle portion within a first partition and a second particle portion within a second partition;
   a creation of a new partition;
   a deletion of an empty partition;
   a consolidation of two or more partitions into a single partition;
   a split of an existing partition into two or more partitions;
   a selective acceptance of an operation based at least in part on a pseudo-temperature;
   a selective acceptance of an operation according to a Metropolis criterion;
   a change in the pseudo-temperature according to a predetermined criterion, a predetermined pattern, or a schedule;
   an operation that is statistically uncorrelated with a preceding operation;
   an operation that is scheduled deterministically; or
   an operation that is scheduled based on criteria reflecting a state of the grand canonical ensemble.

5. The computer-implemented method of claim 1, wherein each partition corresponds to a cluster of the biological samples associated with the particles of the partition; and further comprising extracting features of the cluster that distinguish the cluster of the biological samples from others of the biological samples not within the cluster.

6. The computer-implemented method of claim 1, wherein the iterative improvement procedure is performed using two or more of:
   a Monte Carlo procedure;
   deterministic evolution; or
   processes analogous to grand canonical ensemble phase transitions.

7. The computer-implemented method of claim 1, wherein a given one of the data vectors comprises or is derived from one or more of:
   sequence reads of a single cell of the respective biological sample;
   transcriptome data of the respective biological sample;
   cytometric data of the respective biological sample;
   a medical, physical, disease state, or phenotype attribute of the respective biological sample;
   a medical, physical, or domain-specific attribute of clinical trial or electronic medical record (EMR) data of a patient or human subject; or
   a component representing a measurement of a single cell of the respective biological sample.

8. The computer-implemented method of claim 1 wherein the measures are pseudo-energy measures comprising a weighting function dependent on pseudo-distance between two data vectors in a partition.

9. The computer-implemented method of claim 8, wherein the weighting function has the form of a Lennard-Jones potential, a 6-9 Lennard-Jones potential, a modified Lennard-Jones potential, or a Morse potential.

10. The computer-implemented method of claim 1, wherein the partitions comprise one or more null partitions, and active partitions that are not null partitions.

11. The computer-implemented method of claim 1, wherein the iterative improvement procedure has the following properties:
  each data vector is identified with exactly one particle in the grand canonical ensemble; and
  a first component of a first data vector can be present in at most one partition in the grand canonical ensemble.

12. The computer-implemented method of claim 1, wherein a given one of the biological samples can be represented in more than one of the selected partitions.

13. The computer-implemented method of claim 1, further comprising selecting a group of the biological samples corresponding to one of the selected partitions.

14. The computer-implemented method of claim 1, wherein each data vector comprises at least $10^6$ components, a plurality of the components represent sequence read data, and at least one component indicates a cell state.

15. The computer-implemented method of claim 1, wherein each data vector comprises at least $10^6$ components, a plurality of the components represent gene mutation data, and at least one component indicates a disease cell state.

16. The computer-implemented method of claim 1, further comprising extracting, for at least one of the selected partitions, a set of one or more features associated with respective data vector components, using linear discriminant analysis (LDA).

17. The computer-implemented method of claim 16, further comprising developing or characterizing a cell-based therapy using the extracted set of one or more features.

18. The computer-implemented method of claim 1, further comprising, subsequent to the determining, transmitting data representing the selected partitions and/or the classified biological samples via a computer network.

19. A computer-implemented method for classifying biological samples, comprising:
  forming a plurality of data vectors characterizing respective biological samples, wherein the data vectors in the plurality comprise components representing attributes of the respective biological samples;
  by one or more computer processors having memory attached thereto:
    configuring a multi-partition grand canonical ensemble comprising a plurality of particles, the particles representing the data vectors and thereby associated with the biological samples;
    performing a Monte Carlo procedure on the multi-partition grand canonical ensemble to reduce pseudo-energy of a plurality of partitions of the multi-partition grand canonical ensemble by redistributing the particles and/or the components of the data vectors among the plurality of partitions, wherein the pseudo-energy of a given partition is a measure of similarity between the particles of the given partition, and wherein reduced pseudo-energy corresponds to increased similarity;
    determining, from the Monte Carlo procedure, a set of selected partitions of the particles, each selected partition having reduced pseudo-energy;
  where each partition corresponds to a cluster of the biological samples associated with the particles of the partition; and
  extracting features of the cluster that distinguish the cluster of the biological samples from others of the biological samples not within the cluster.

20. One or more computer-readable media storing instructions which, when executed by one or more hardware processors, cause the one or more hardware processors to perform operations comprising:
  obtaining a plurality of data vectors characterizing respective biological samples and comprising components representing attributes of the respective biological samples, wherein at least one of the components indicates a disease state or a state conferring efficacy for treating a disease or condition;
  obtaining one or more measures representative of similarity between data vectors of the plurality of data vectors;
  performing an iterative improvement procedure on a grand canonical ensemble comprising a plurality of particles variably distributed among one or more partitions, the particles representing respective data vectors of the plurality of data vectors, wherein the iterative improvement procedure comprises simulated annealing and enhances the one or more measures;
  determining, from the iterative improvement procedure, a set of selected partitions of the particles having increased similarity between the data vectors of the particles in each selected partition;
  extracting, for at least one of the selected partitions, features associated with respective ones of the components; and
  outputting the features for therapeutic development.

* * * * *